US007799794B2

(12) United States Patent
Kivlighn et al.

(10) Patent No.: US 7,799,794 B2
(45) Date of Patent: Sep. 21, 2010

(54) TREATMENT FOR CARDIOVASCULAR DISEASE

(75) Inventors: Salah Kivlighn, Doylestown, PA (US); Richard Johnson, Bellaire, TX (US); Marilda Mazzali, Houston, TX (US)

(73) Assignees: Merck Sharp & Dohme Corp., Rahway, NJ (US); University of Washington, Seattle, WA (US)

( * ) Notice: Subject to any disclaimer, the term of this patent is extended or adjusted under 35 U.S.C. 154(b) by 474 days.

(21) Appl. No.: 09/892,505

(22) Filed: Jun. 28, 2001

(65) Prior Publication Data

US 2002/0019360 A1 Feb. 14, 2002

Related U.S. Application Data

(60) Provisional application No. 60/214,825, filed on Jun. 28, 2000.

(51) Int. Cl.
*A61K 31/519* (2006.01)
(52) U.S. Cl. ............... 514/262.1; 514/183; 514/256
(58) Field of Classification Search ........... 514/262, 514/264, 262.1, 183
See application file for complete search history.

(56) References Cited

U.S. PATENT DOCUMENTS

| 4,032,522 | A | * | 6/1977 | Baldwin et al. | 544/405 |
|---|---|---|---|---|---|
| 4,058,614 | A | * | 11/1977 | Baldwin | 514/341 |
| 4,296,122 | A | | 10/1981 | Cragoe, Jr. et al. | 424/285 |
| 4,510,322 | A | | 4/1985 | Blaine et al. | 514/255 |
| 4,539,323 | A | * | 9/1985 | Mentrup et al. | 514/266.22 |
| 5,260,322 | A | | 11/1993 | Nakasima et al. | |
| 5,747,495 | A | * | 5/1998 | Maeda et al. | 514/262.1 |

FOREIGN PATENT DOCUMENTS

| DE | 2707269 | 2/1977 |
|---|---|---|
| DE | 2707270 | 2/1977 |
| EP | 000128 | 6/1978 |
| EP | 0 104483 | 8/1983 |
| EP | 0 337 350 A2 | 10/1989 |
| EP | 415566 | 7/1990 |
| GB | 1 451 029 | 9/1976 |
| WO | WO 93 04688 | 3/1993 |
| WO | WO 00 07629 | 2/2000 |

OTHER PUBLICATIONS

Proceedings of the Society for Experimental Biology and Medicine 1996, 211(4), 366-73.*
Ward, Lancet 1988, 352, pp. 670-671.*
L.M. Burrell, "A risk-benefit assessment of Losartan potassium in the treatment of hypertension", Drug Safety, vol. 16, No. 1, 1997, pp. 56-65.
T. Gibson E.A.; "Tienilic acid in the treatment of gout and hypertension", Advances in Experimental Medicine and Biology, vol. 122A, 1980 pp. 277-282.
Wu, X. et al; Two Independent Mutational Events Resulted in the Loss of Urate Oxidase During Hominoid Evolution, J. Mol. Evol. 34:78-84 (1992).
Eaton, S.B. et al; a Consideration of its Nature and Current Implications, N. Engl J Med 312:283-289 (1985).
Cannon, P.J. et al; Hyperuricemia in Primary and Renal Hypertension, N Engl J Med 275:457-464 (1966).
Haig, A., On Uric Acid and Arterial Tension, Br Med J 1:288-291 (1889).
Selby, J.V. et al, Precursors of Essential Hypertension: Pulmonary Function, Heart Rate, Uric Acid, Serum Cholesterol, and Other Serum Chemistries, Am J Epidemiol 131:1017-27 (1990).
Jossa, F. et al, Erum Uric Acid and Hypertension:The Olivetti Heart Study, J Hum Hypertens 8:677-681 (1994).
Goldstein, H.S. et al, Relationship Between Serum Uric Acid and Blood Pressure in Adolescents, Annals Hum Biol 20:423-431(1993).
Fang, J. et al, Serum Uric Acid and Cariovascular Mortality, The NHANES I Epidemiologic Follow-up Study, 1971-1992, JAMA 283:2404-2410 (2000).
Bengtsson, C. et al, Hyperuricemia and Risk of Cardiovascular Disease and Overall Death, Acta Med Scand 224:549-55 (1988).
Alderman, M.H. et al, Serum Uric Acid and Cariovascular Events in Successfully Treated Hypertensive Patients, Hypertension 34:144-150 (1999).
Lehto, S. et al, Serum Uric Acid is a Strong Predictor of Stroke in Patients with Non-Insulin Dependent Diabetes Mellitus, Stroke 29:635-639 (1998).
Persky, V.W. et al, Uric Acid:A risk Factor for Coronary Heart Disease? Circulation 59:969-979 (1979).
Vaccarino, V. et al, Risk Factors for Cardiovascular Disease: One Down, Many More to Evaluate, Ann Int Med 131:62-63 (1999).
Wannamethee, S.G., Is Serum Uric Acid a Risk Factor for Coronary Heart Disease? J Hum Hypertens 13:153-156 (1999).
R. Grahame et al., "Clinical survey of 354 patients with gout", Arm. Rheum. Dis. (1970), 29, pp. 461-468.
Bruce F. Culleton, MD, et al., "Serum Uric Acid and Risk for Cardiovascular Disease and Death: The Framingham Heart Study", Ann Intern Med.,1999, 131, pp. 7-13.
Ronald Klein, MD, et al., Serum Uric Acid: Its Relationship to Coronary Heart Disease Risk Factors and Cardiovascular Disease, Evans, County, Georgia, Arch Intern Med/ vol. 132, Sep. 1973, pp. 401-410.
Katsuhido Yano, et al., Ten-Year Incidence of Coronary Heart Disease in the Honolulu Heart Program, American Journal of Epidemiology, vol. 119, No. 5, May 1984, pp. 653-665.

(Continued)

*Primary Examiner*—Sreeni Padmanabhan
*Assistant Examiner*—Shobha Kantamneni
(74) *Attorney, Agent, or Firm*—Timothy H. Van Dyke; Beusse Wolter Sanks Mora & Maire

(57) ABSTRACT

This invention relates to a method for treating and preventing hypertension by administering a therapeutically effective amount of an agent capable of reducing uric acid levels in a patient in need of such treatment. Additionally, the scope of the invention includes a method of treating coronary heart disease by administering a therapeutically effective amount of an agent capable of reducing uric acid levels in a patient in need of such treatment.

1 Claim, 12 Drawing Sheets

OTHER PUBLICATIONS

"Chronic cyclosporine nephropathy: The Achilles' heel of immunosuppressive therapy", Kidney International, vol. 50, 1996, pp. 1089-1100.

Bryan D. Myers et al., "Cyclosporine-Induced Chronic Nephropathy: An Obliterative Microvascular Renal Injury", Journal of the American Society of Nephrology, vol. 2, Supplement 1, 1991, pp. 45-52.

J.R. Chapman et al., Reversibility of Cyclosporin Nephrotoxicity After Three Months' Treatment, the Lancet, Jan. 19, 1985, pp. 128-129, 308-313.

Paul R. Gores, M.D., et al., "Hyperuricemia After Renal Transplantation", The American Journal of Surgery, vol. 156, Nov. 1988, pp. 397-400.

Leslie E. Kahl, M.D. et al., "Gout in the Heart Transplant Recipient: Physiologic Puzzle and Therapeutic Challenge", The American Journal of Medicine, vol. 87, Sep. 1989, pp. 289-294.

David E.R.Sutherland et al., "Results of the Minnesota Randomized Prospective Trial of Cyclosporine Versus Azathioprine-Antilymphocyte Globulin for Immunosuppression in Renal Allograft Recipients", American Journal of Kidney Diseases, vol. V, No. 6, Jun. 1985, pp. 318-327.

Cynthia West, MD, et al., "The Incidence of Gout in Renal Transplant Recipients", American Journal of Kidney Disease, vol. X, No. 5, Nov. 1987, pp. 369-371.

R.M. Zurcher, et al., "Hyperuricaemia in cyclosporin-treated patients: a GFR-related effect", 1996 European Dialysis and Transplant Association-European Renal Association, 1996, 11: pp. 153-158.

Jarmo Laine, et al., "Mechanisms of Hyperuricemia in Cyclosporine-Treated Renal Transplanted Children", Nephron, 1996, 74: pp. 318-323.

R. Marcen et al., "Impairment of Tubular Secretion of Urate in Renal Transplant Patients on Cyclosporine", Nephron 1995, 70:, pp. 307-313.

Bryan D. Myers, "Cyclosoporine nephrotoxicity", Kidney International, vol. 30, 1986, pp. 964-974.

W.M. Bennett, et al., "Nephrotoxicity of immunosuppressive drugs"., Nephrol Dial Transplant, 1994 9, Supp. 4:, pp. 141-145.

Emmanuel A. Burdmann, et al., "Prevention of experimental cyclosporin-induced interstitial fibrosis by losartan and enalapril", The American Physiological Society, 1999, pp. F194-499.

Raimund H. Pichler[2], et al., "Pathogenesis of Cyclosporine Nephropathy: Roles of Angiotensin II and Osteopontin", Journal of American Society of Nephrology, vol. 6, No. 4, 1995, pp. 1186-1196.

Peter F. Hoyer, et al., "Renal handling of uric acid under cyclosporin A treatment", Pediatric Nephrology, 1988, 2, pp. 18-21.

Franz H. Messerli, M.D., et al., "Serum Uric Acid in Essential Hypertension: An Indicator of Renal Vascular Involvement", Annals of Internal Medicine, 1980, 93: pp. 817-821.

Laurence H. Beck, "Requeim for gouty nephropathy", Kidney International, vol. 30, 1986, pp. 280-287.

"An evaluation of the pathogenesis of the gouty kidney", Kidney Interntational, vol. 8, 1975, pp. 65-71.

Richard J. Johnson, M.D., et al. "Reappraisal of the Pathogenesis and Consequences of Hyperuricemia in Hypertension, Cardiovascular Disease, and Renal Disease", American Journal of Kidney Diseases, vol. 33, No. 2, Feb. 1999, pp. 225-234.

V. Nickeleti et al., "Uric acid nephropathy and end-stage renal disease—Review of a nono-disease", Nephrol Dial Transplant, 1997, 12, pp. 1832-1838.

Ts'ai-Fan Yü, M.D., "Renal Function in Gout: V. Factors Influencing the Renal Hemodynamics", The American Journal of Medicine, Nov. 1979, vol. 67, pp. 766-771.

Sônia M. A. Assis[2], et al., L-Arginine and Allopurinol Protect Against Cyclosporine Nephrotoxicity[1], Transplantation, vol. 63, Apr. 27, 1997, vol. 63, pp. 1070-1073.

Bernhard F. Becker, Towards the Physiological Function of Uric Acid, Free Radical Biology and Medicine, vol. 14, 1993, pp. 615-631.

Jerry Waisman, M.D., A Preliminary Report of Nephropathy in yperuricemic Rats, Laboratory Investigation, vol. 30, No. 6, 1974, pp. 716-722.

Harvey C. Gonick, M.D., "The Renal Lesion in Gout", vol. 62, No. 4, Apr. 1965, pp. 667-674.

Lawrence Berger, M.D., et al., "Renal Function in Gout:IV. An Analysis of 524 Gouty Subjects Including Long-Term Follow-Up Studies*", The American Journal of Medicine, vol. 59, Nov. 1975, pp. 605-613.

David Greenbaum, M.B., M.R.C.P., "Renal Biopsy in Gout", British Medical Journal, May 27, 1961, pp. 1502-1504.

Ts'ai-Fan Yü, M.D., et al., "Impaired Renal Function in Gout" Its Association with Hypertensive Vascular Disease and Intrinsic Renal Disease , The American Journal of Medicine, vol. 72, Jan. 1982, pp. 95-100.

F. Perez-Ruiz, et al., "Efficacy of allopurinol and benzbromarone for the control of hyperuricaemia. A pathogenic approach to the treatment of primary chronic gout", Am. Rheum. Dis., 1995, 57, pp. 545-549.

W. Jeffrey Fessel, M.D., Renal Outcomes of Gout and Hyperuricemia, The American Journal of Mediciine, vol. 67, Jul. 1979, pp. 74-82.

Alderman, M.H. et al, "Serum Uric Acid and Cariovascular Events in Successfully Treated Hypertensive Patients", Hypertension 34:144-150 (1999).

Fang, J. et al, "Serum Uric Acid and Cariovascular Mortality", The NHANES I Epidemiologic Follow-up Study, 1971-1992, JAMA 283:2404-2410 (2000).

Landmesser, U. et al., "Oxidative stress and vascular damage in hypertension", Coronary Artery Disease, Sep. 2001, 12, (6): 455-461.

Maxwell, Simon et al., "Anti-oxidants—a protective role in cardiovascular disease?", Expert Opinion, Pharmacother., Nov. 2001; 2(11): 1737-1750.

Nakashima, M., "Pilot study of the uricosuric effect of DuP-753, a new angiotensin II receptor antagonist, in healthy subjects", Eur J. Clin Pharmacol (1992), 42: 333-335.

Nakazono, K. et al., "Does superoxide underlie the pathogenisis of hypertension?", Proc. Natl. Acad. Sci., 88: 10045-10048, 1991.

Pui, Ching-Hon et al., "Recombinant Urate Oxidase for the Prophylaxis or Treatment of Hyperuricemia in Patients With Leukemia or Lymphoma", J. Clin. Oncol., (2001), 19: 697-704.

Sowers, J.R., "Hypertension, Angiotensis II, and Oxidative Stress", NEJM, 346: (2002), 1999-2001.

Vaziri, N.D. et al., "Effect of Antioxidant Therapy on Blood Pressure and NO Synthase Expression in Hypertensive Rats", American Heart Association, 36: (2000) 957-964.

Verdecch ia, P. et al., "Relation Between Serum Uric Acid and Risk of Cardiovascular Disease in Essential Hypertension: The PIUMA Study", American Heart Association, 36: (2000) 1072-1078.

Wilox, C.S., "Reactive Oxygen Species: Roles in Blood Pressure and Kidney Function", Current Hypertension Reports, 2002, 160-6.

Miyamoto, Y., et al. "Potentiation of nitric oxide-mediated vasorelaxation by xanthine oxidase inhibitors.", Proceedings of the Society for Experimental Biology and Medicine, Apr. 1996, vol. 211, NR 4, p. 366-373.

* cited by examiner

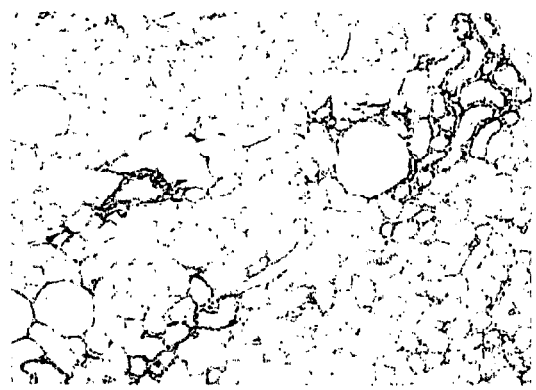
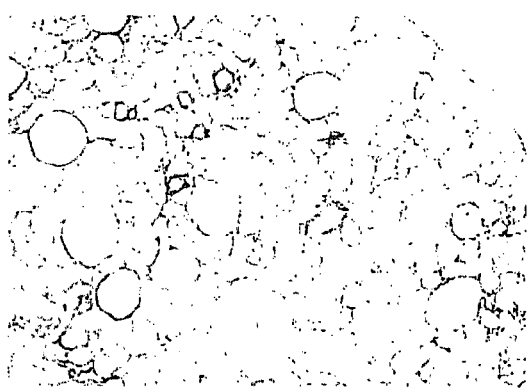
FIG.6A  FIG.6B
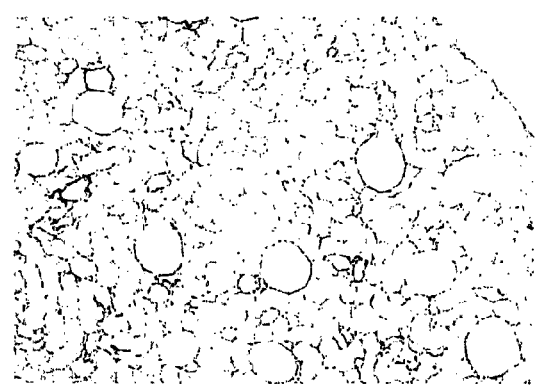
FIG.6C

TREATMENT FOR CARDIOVASCULAR DISEASE

BACKGROUND OF THE INVENTION

This application claims priority from co-pending provisional application Serial No. 60/214,825 filed on Jun. 28, 2000.

The U.S. Government has a paid-up license in this invention and a right in limited circumstances to require the patent owner to license others on reasonable terms as provided for by the terms of National Institute of Health Grant No. DK 47659.

Uric acid is a purine metabolite that in most animals is degraded by the hepatic enzyme uricase to allantoin. However, several mutations of the gene for this enzyme occurred during early primate development with the consequence that man and other primates have relatively higher levels of serum uric acid [Wu, X., Muzny, D. M., Lee, C. C., and Caskey, C. T., Two independent mutational events resulted in the loss of urate oxidase during hominoid evolution. *J Mol. Evol.* 34:78-84 (1992)]. The adaptive benefit of this deletion is not known nor has the modern day consequences of these mutations been fully understood. It has been hypothesized that the loss of uricase provided a protective benefit to prehistoric man who was known to have a very low sodium diet [Eaton, S. B., Konner, and M., Paleolithic nutrition: A consideration of its nature and current implications. *N Engl J Med* 312: 283-289 (1985)] but in modem times these mutations resulted in the development of hypertension and other cardiovascular diseases. In most subjects, the loss of uricase appears to be of no significance, but for the 10 to 15 percent of the general population with the highest uric acid levels (>6.0 mg/dl in women and >6.5mg/dl in men), there is an increased risk for the development of hypertension, atherosclerosis, and other cardiovascular diseases. Additionally 25 to 50% of hypertensive individuals have elevated serum uric acid, based upon the current standards 7 mg/dl [Cannon, P. J., Stason, W. B., Demartini, F. E., Sommers, S. C., and Laragh, J. H., Hyperuricemia in primary and renal hypertension. *N Engl J Med* 275:457-464 (1966]. This invention demonstrates for the first time mechanistic evidence that uric acid is directly related to the development of increased blood pressure.

An association between an elevated uric acid and an increased risk for cardiovascular disease was originally suggested by Haig in the late 1800s. Haig postulated that uric acid crystals might precipitate in the circulation and occlude the microvasculature [Haig, A., On uric acid and arterial tension. *Br Med J* 1:288-291 (1889)], thereby assuming that the damaging effects of uric acid were related to the formation of uric acid crystals and not to the soluble form of uric acid. Recent epidemiological studies have reported that an elevated uric acid confers an increased risk for the development of hypertension [Selby, J. V., Friedman, G. D., and Quesenberry, C. P., Precursors of essential hypertension: pulmonary function, heart rate, uric acid, serum cholesterol, and other serum chemistries. *Am J Epidemiol* 131:1017-27 (1990); Jossa, F., et al. Serum uric acid and hypertension: the Olivetti heart study. *J Hum Hypertens* 8:677-681 (1994); and Goldstein, H. S., and Manowitz, P., Relationship between serum uric acid and blood pressure in adolescents. *Annals Hum Biol* 20:423-431 (1993)], ischemic heart disease [Fang, J., and Alderman, M. H. Serum uric acid and cardiovascular mortality. The NHANES I Epidemiologic Follow-up Study, 1971-1992 *JAMA* 283:2404-2410 (2000); Bengtsson, C., Lapidus, L., Stendahl, C., and Waldenström, J., Hyperuricemia and risk of cardiovasular disease and overall death. *Acta Med Scand* 224:549-55 (1988); and Alderman, M. H., Cohen, H., Madhavan, S., Kivlighn, S. Serum uric acid and cardiovascular events in successfully treated hypertensive patients. *Hypertension* 34:144-150 (1999).], and stroke [Lehto, S., Niskanen, L., Rönnemaa, T., and Laakso, M., Serum uric acid is a strong predictor of stroke in patients with non-insulin dependent diabetes mellitus. *Stroke* 29:635-639 (1998)]. In the Worksite study an increase of 1 mg/dl of uric acid conferred the same cardiovascular risk as an increase of 10 mm Hg in systolic blood pressure or 20 mg/dl of cholesterol [Alderman, M. H., Cohen, H., Madhavan, S., and Kivlighn, S., Serum uric acid and cardiovascular events in successfully treated hypertensive patients. *Hypertension* 34:144-150 (1999).]. Several studies have also reported that the increased mortality associated with diuretic use can be attributed to the increase in uric acid induced by these agents [Franse, L. V., Pahor, M., and Barli, M. D., Serum uric acid, it's change with diuretic use and risk of cardiovascular events in the Systolic Hypertension in the Elderly Program (SHEP). *American Society of Hypertension Annual Meeting*, May 1999, New York.]. Others have shown that an increased uric acid confers increased risk for cardiovascular mortality, especially in women [Fang, J., and Alderman, M. H., Serum uric acid and cardiovascular mortality. The NHANES I Epidemiologic Follow-up Study, 1971-1992 *JAMA* 283:2404-2410 (2000); Bengtsson, C., Lapidus, L., Stendahl, C., and Waldenström, J., Hyperuricemia and risk of cardiovasular disease and overall death. *Acta Med Scand* 224:549-55 (1988); and Persky, V. W., et al. Uric acid: A risk factor for coronary heart disease? *Circulation* 59:969-979 (1979)]. Despite the clinical and epidemiological evidence, some authorities do not consider an elevated uric acid to be a true cardiovascular risk factor [Vaccarino, V., and Krumholz, H. M., Risk factors for cardiovascular disease: One down, many more to evaluate. *Ann Int Med* 131:62-63 (1999); and Wannamethee, S. G., Is serum uric acid a risk factor for coronary heart disease? *J Hum Hypertens* 13:153-156 (1999)]. This is because many patients with an elevated uric acid have other well-established risk factors for cardiovascular disease, such as hypertension, renal disease, obesity, dyslipidemia, and insulin resistance [Barlow, K. A., Hyperlipidemia in primary gout. *Metabolism* 17:289-299 (1968) and Grahame, R., and Stott, J. T., Clinical survey of 354 patients with gout. *Ann Rheum Dis* 29:461-468 (1970)]. Whereas some studies have found that an elevated uric acid level is an independent risk factor after controlling for the contribution of these other risk factors by multivariate analyses [Fang, J., and Alderman, M. H., Serum uric acid and cardiovascular mortality. The NHANES I Epidemiologic Follow-up Study, 1971-1992 *JAMA* 283:2404-2410 (2000); Bengtsson, C., Lapidus, L., Stendahl, C., and Waldenström, J. Hyperuricemia and risk of cardiovasular disease and overall death. *Acta Med Scand* 224:549-55 (1988); and Persky, V. W., et al. Uric acid: A risk factor for coronary heart disease? *Circulation* 59:969-979 (1979)], other studies including the recent Framingham analysis could not [Culleton, B. F., Larson, M. G., Kannel, W. B., and Levy, D., Serum uric acid and risk for cardiovascular disease and death: The Framingham Study. *Ann Intern Med* 131:7-13 (1999); Klein, R., et al. Serum uric acid: its relationship to coronary heart disease risk factors and cardiovascular disease. Evans County, Georgia. *Arch Int Med* 132:401-410 (1973); and Yano, K., Reed, D. M., and McGee, D. L., Ten year incidence of coronary heart disease in the Honolulu Heart Program: relationship to biologic and lifestyle characteristics. *Am J Epidemiol* 119:653-666 (1984).]. The lack of a mechanistic pathway by which uric acid can cause cardiovascular disease, coupled with the inconclusive clinical and epidemiological data, have left this issue unresolved. In considering this controversy, it is important to note that no animal model existed to study the effects of a mildly elevated uric acid.

Cyclosporine (CSA) was introduced in the 1980's as an immunosuppressant, and quickly become a first line treatment in organ transplantation as well as in other immunologically mediated diseases [Bennett, W. M., De Mattos, A., Meyer, M. M., Andoh, T. F., and Barry, J. M., Chronic cyclosporine nephropathy. The Achille's heel of immunossupressive therapy. *Kidney Int* 1996; 50:1089.]. Cyclosporine has numerous side effects, of which two of the most important are nephrotoxicity [Myers, B. D. and Newton, L., Cyclosporine induced chronic nephropathy: an obbliterative microvascular renal injury. *J Am Soc Nephrol* 1991; 2: S45, and Chapman, J. R., Harding, N. G. L., Griffiths, D., and Morris, P. J., Reversibility of cyclosporine nephrotoxicity after three months treatment. *Lancet* 1985; 1:128.] and hyperuricemia [Gores, P. F., Fryd, D. S., Sutherland D. E. R., Najarian, J. S., and Simmons, R. L., Hyperuricemia after renal transplantation. *Am J Surg* 1988;156: 397.]. As many as 50% of patients taking CSA develop hyperuricemia [Kahl, L. E., Thompson, M. E., and Griffith, B. P., Gout in the heart transplant recipient: Physiological puzzle and therapeutic challenge. *Am J Med* 1989; 87: 289, Najarian, J. S., Fryd, D. S., and Stransd, M., A single institution, randomized, prospective trial of cyclosporine versus azathioprine-antilymphocyte globulin for immunossupression in renal allograft recipients. *Ann Surg* 1985; 201:142 and Sutherland, D. E. R., Fryd, D. S., and Strand, M. H., Minnesota randomized prospective trial of cyclosporine versus azathioprine-antilymphocyte globulin for immunossupression in renal allograft recipients. *Am J Kidney Dis* 1985; 5:318.] and 9 to 10% develop gout [West, C., Carpenter, B. J., and Hakala, T. R., The incidence of gout in renal transplant recipients. *Am J Kidney Dis* 1987; 10: 369.]. The hyperuricemia from CSA is thought to result from both a decrease in GFR [Zurcher, R. M., Bock, H. A., and Thiel, G., Hyperuricemia in cyclosporine treated patients: A GFR related effect. *Nephrol Dial Transplant* 1996; 11:153.], as well as an increase in net tubular urate reabsorption [Laine, J., and Holmberg, C., Mechanisms of hyperuricemia in cyclosporine-treated renal transplanted children. *Nephron* 1996; 74: 318, and Marcen, R., Gallego, N., Orofino, L. et al., Impairment of tubular secretion of urate in renal transplant patients on cyclosporine. *Nephron* 1995; 70: 307.]. The most important complication of CSA is nephrotoxicity, which is characterized histologically by striped interstitial fibrosis, tubular atrophy and arteriolar hyalinosis [Bennett, W. M., De Mattos, A., Meyer, M. M., Andoh, T. F., and Barry, J. M., Chronic cyclosporine nephropathy. The Achille's heel of immunossupressive therapy. Kidney Int 1996; 50:1089, Myers, B., Cyclosporine nephrotoxicity. *Kidney Int* 1986; 30:964, and Bennett, W. M., Burdmann, E. A., Andoh, T. F., Houghton, D. C., Lindsley, J., and Elzinga, L. W., Nephrotoxicity of immunossupressive drugs. *Nephrol Dial Transplant* 1994; 9:141.]. The pathogenesis of CSA nephropathy is multifactorial but likely involves afferent arteriolar vasoconstriction with activation of the renin angiotensin pathway and inhibition of nitric oxide (NO) production [Bennett, W. M., Burdmann, E. A., Andoh, T. F., Houghton, D. C., Lindsley, J., and Elzinga, L. W.: Nephrotoxicity of immunossupressive drugs. *Nephrol Dial Transplant* 1994; 9:141, Burdmann, E. A., Andoh, T. F., Nast, C. C., et al., Prevention of experimental cyclosporine induced interstitial fibrosis by losartan and enalapril. *Am J Physiol* 1995; 269: F491, and Pichler, R., Franceschini, N., Young, B. A. et al., Pathogenesis of cyclosporine nephropathy. Roles of angiotensin II and osteopontin. *J Am Soc Nephrol* 1995; 6: 1186.].

The possibility that cyclosporine induced hyperuricemia may have a role in either mediating or exacerbating cyclosporine nephropathy has not previously been considered. However, it is known that hyperuricemia is also associated with reduced renal blood flow and increased renal vascular resistance [Hoyer, P. F., Lee, I. K., Oemar, B. S., Krohn, H. P., Offner, G., and Brodhel, J., Renal handling of uric acid under cyclosporine A treatment. *Pediatr Nephrol* 1988; 2:18, and Messerli, F. H., Frolich, E. D., Drelinski, G. R., Suarez, D. H., and Aristimuno, G. G., Serum uric acid in essential hypertension: an indicator of renal vascular involvement. *Ann Int Med* 1980; 93:817.] and those patients with long-standing gout may develop chronic tubulointerstitial disease [Beck, L. H., Requiem for gouty nephropathy. *Kidney Int* 30:280-287, 1986, Emmerson, B. T., and Row, P. G., An evaluation of the pathogenesis of the gout kidney. *Kidney Int.* 1975; 8:65, and Johnson, R. J., Kivlighn, S. D., Kim, Y. G., Suga, S., and Fogo, A. B., Reapprasial of the pathogenesis and consequences of hyperuricemia in hypertension, cardiovascular disease and renal disease. *Am J Kidney Dis* 1999; 33: 225.]. Controversy has existed, however, over whether hyperuricemia is the cause or consequence of renal vasoconstriction and tubulointerstitial lesions [Nickeleit, V., and Mihatsh, M. J., Uric acid nephropathy and end-stage renal disease. Review of a non-disease. *Nephrol Dial Transplant* 1997;12: 1832, and Yü, T., Berger, L., Dorph, D. J., and Smith, H., Renal function in gout: V- Fators influencing the renal hemodynamics. *Am J Med* 1979: 67:766.].

A recent report suggested that allopurinol, an inhibitor of uric acid production, could protect the kidney from CSA nephrotoxicity [Assis, S. M., Monteiro, J. L., and Seguro, A. C., L-arginine and allopurinol protect against cyclosporine nephrotoxicity. *Transplantation* 1997; 63(8): 1070.]. Thus the hypothesis that hyperuricemia might exacerbate cyclosporine nephropathy was tested. As rodents normally do not become hyperuricemic because they have the hepatic enzyme uricase, which degrades uric acid to allantoin [Becker, B. F., Towards the physiological function of uric acid. *Free Rad Biol Med* 1993; 14:615, and Waisman, J., Bluestone, R. and Klinemberg, J. R., A preliminary report of nephropathy in hyperuricemic rats. *Lab Invest* 1974; 30:716.], rats with cyclosporine nephropathy, in the presence and absence of the uricase inhibitor, oxonic acid were compared. This invention demostrates that hyperuricemia exacerbates CSA nephropathy through a crystal independent mechanism.

Hyperuricemia, defined as serum uric acid levels >7.0 mg/dl in man and >6.0 mg/dl in women, is a common metabolic abnormality that is observed in 4 to 6% of the population (Wyngaarden J. B. and Kelley W. N., Epidemiology of hyperuricemia and gout. *In Gout and Hyperuricemia*, Grune and Stratton, New York, 1976, pp 21-37.). The major risks classically attributed to hyperuricemia have been the risk of developing gout and/or uric acid renal stones. Patients with longstanding hyperuricemia and/or gout are also at risk for developing chronic renal disease (Talbot, J. H., and Terplan, K. L., The kidney in gout. *Medicine* 39:405-467, 1960, and Gonick, H. C., Rubini, M. D., Gleason, I. O., and Sommers, S. C., The renal lesion in gout. *Ann Int Med* 62:667-74, 1965.). Several large studies have documented that between 30 and 60% of patients with gout will develop renal insufficiency and up to 10% will develop end stage renal disease (Talbot, J. H., and Terplan, K. L., The kidney in gout. *Medicine* 39:405-467, 1960; Gonick, H. C., Rubini, M. D., Gleason, I. O., and Sommers, S. C., The renal lesion in gout. *Ann Int Med* 62:667-74, 1965; Yü, T., Berger, L., Dorph, D. J., and Smith, H., Renal function in gout: V- Factors influencing the renal hemodynamics. *Am J Med* 67:766-71, 1979; and Berger, L., and Yü, T., Renal Function in Gout: IV. An Analysis of 524 Gouty Subjects Including long-term follow-up studies. *Am J Med* 59:605-613, 1975). Renal structural changes are even more common than the functional abnormalities (Greenbaum, D., and Ross, J. H., Renal biopsy in gout., *Brit Med J* 1:1502-1504, 1961.), and in one study renal disease was observed in 287 of 290 patients with gout (Talbot, J. H., and Terplan, K. L., The kidney in gout. *Medicine* 39:405-467, 1960.). The renal disease, which has been termed 'gouty nephropathy', is characterized by chronic tubulointerstitial fibrosis, often with arteriolosclerosis and glomerular sclerosis (Talbot, J. H., and Terplan, K. L., The kidney in gout. *Medicine* 39:405-467, 1960). In addition, many biopsies show focal deposits of urate crystals, particularly in the outer medulla (Talbot, J. H., and Terplan, K. L., The kidney in gout. *Medicine* 39:405-467, 1960; Gonick, H. C., Rubini, M. D., Gleason, I. O., and Sommers, S. C., The renal lesion in gout. *Ann Int Med* 62:667-74, 1965; and Cannon, P. J., Stason, W. B., Dematini, F. E., Sommers, S. C., and Laragh, J. H., Hyperuricemia in Primary and Renal Hypertension. *New Engl J Med* 275:457-464, 1966.).

However, investigators have challenged if 'gouty nephropathy' truly exists (Beck, L. H., Requiem for gouty nephropathy. *Kidney Int* 30:280-287, 1986, and Nickeleit, V. and Mihatsh, M. J., Uric acid nephropathy and end-stage renal disease. Review of a non-disease. *Nephrol Dial Transplant* 12: 1832-38, 1997.). Some studies have suggested that the renal functional changes could be attributed to co-existing hypertension or the consequence of aging (Yü, T., Berger, L., Dorph, D. J., and Smith, H., Renal function in gout: V- Factors influencing the renal hemodynamics. *Am J Med* 67:766-71, 1979, and Yü, T. and Berger, L., Impaired Renal Function in Gout: Its Association with Hypertensive Vascular Disease and Intrinsic Renal Disease. *Am J Med* 72:95-100, 1982). Others have noted the apparent discrepancy between the focal nature of the urate deposits and the diffuse interstitial disease ((Beck, L. H., Requiem for gouty nephropathy. *Kidney Int* 30:280-287, 1986, and Nickeleit, V. and Mihatsh, M. J., Uric acid nephropathy and end-stage renal disease. Review of a non-disease. *Nephrol Dial Transplant* 12: 1832-38, 1997.). Furthermore, the effect of uric acid lowering agents on improving renal function in patients with gout has been variable, with both positive (Perez-Ruiz, F., Calabozo, M., Fernandez-Lopez, M. J., Herrero-Beites, A., Ruiz-Lucea, E., Garcia-Erasukin, G., Duruelo, J., and Alonso-Ruiz, A., Treatment of chronic gout in patients with renal fundction impairment. An open, randomized actively controlled study. *J Clin Rheumatol* 1999; 5:49-55, and Perez-Ruiz F, Alonso-Ruiz A, Calabozo M, Herrero-Beites A, Garcia-Erauskin G, and Ruiz-Lucca E., Efficacy of allopurinol and benzbromarone for the control of hyperuricemia. A pathogenic approach to the treatment of primary chronic gout. *Ann Rheum Dis* 1998; 57:545-549.) and negative (Fessel, W. J., Renal Outcomes of Gout and Hyperuricemia. *Am J Med* 67:74-82, 1979, and Rosenfeld, J. B., Effect of long-term allopurinol administration on serial GFR in normotensive and hypertensive hyperuricemic subjects. *Adv Exp Med Biol* 41B:581-596, 1974) studies reported.

A novel pathway has been demonstrated where uric acid, a purine metabolite present in the blood, actually causes hypertension and renal disease. It is known that markedly elevated uric acid can crystallize in the tubules of the kidney and cause kidney failure. The invention disclosed herein is that mildly elevated uric acid levels can also cause renal disease and hypertension. Furthermore, it has been shown that this action is mediated in part by activation of the renin-angiotensin system in the kidney and by the inhibition of nitric oxide synthases (NOS) within the kidney.

SUMMARY OF THE INVENTION

This invention relates to a method for treating and preventing hypertension by administering a therapeutically effective amount of an agent capable of reducing uric acid levels in a patient in need of such treatment. Additionally, the scope of the invention includes a method of treating coronary heart disease by administering a therapeutically effective amount of an agent capable of reducing uric acid levels in a patient in need of such treatment. The agent, or pharmaceutically acceptable salt thereof, capable of reducing uric acid levels is selected from the group consisting of gene therapy, a xanthine oxidase inhibitor, a uricosuric agent, supplements of the uricase protein and a urate channel inhibitor or combinations thereof. Also within the scope of the invention is a pharmaceutical composition, comprising a renin angiotensin system (RAS) inhibitor, or pharmaceutically acceptable salt thereof and the agent, or pharmaceutically acceptable salt thereof capable of reducing uric acid levels, and a pharmaceutical carrier, or a combination therapy comprising the concomitant, simultaneous or sequential administration of the RAS inhibitor, or pharmaceutically acceptable salt thereof, and the agent, or pharmaceutically acceptable salt thereof, capable of reducing uric acid levels.

BRIEF DESCRIPTION OF THE DRAWINGS

The file of this patent contains at least one drawing executed in color. Copies of this patent with color drawing(s) will be provided by the Patent and Trademark Office upon request and payment of the necessary fee.

FIG. 3—Hyperuricemia Maintains and Elevates Blood Pressure in Rats on a Low Salt diet. Control rats placed on a mild salt restriction (0.125% NaCl diet) have a fall in blood pressure after several weeks; this is prevented in the presence of oxonic acid (2%). Rats placed on oxonic acid and low salt diet that are also administered allopurinol do not show the increase in blood pressure.

FIG. 6—Renal Fibrosis Develops in Hyperuricemic Rats. Rats treated with oxonic acid (2%) and a low salt diet for 11 weeks develop significant striped interstitial fibrosis, as shown by immunostaining for interstitial type III collagen (FIG. 6A). Control rats on a low salt diet do not develop any evidence of interstitial disease (FIG. 6B). Renal fibrosis was less in oxonic acid-treated rats in which allopurinol was administered for 4 weeks prior to sacrifice (FIG. 6C).

DETAILED DESCRIPTION OF THE INVENTION

Figure 1A:
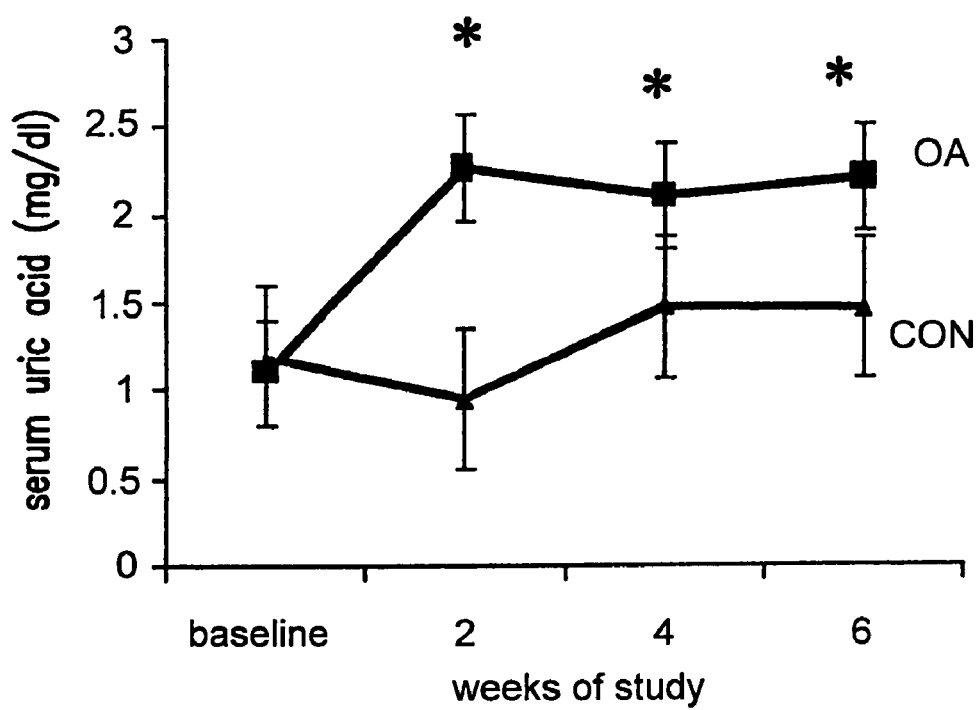
FIG. 1—A Model of Mild Hyperuricemia in Rats. Rats treated with oxonic acid (2%) develop mild hyperuricemia compared to controls on a normal salt diet (FIG. 1A). Light microscopy (PAS, 50×) at 7 weeks is normal (FIG. 1B) and no urate crystals are present by DeGalantha (50×) stain of 100% ethanol-fixed tissue (FIG. 1C). For comparison, we have included a DeGalantha stain in rats with acute urate nephropathy showing intratubular urate crystals (FIG. ID). [Key: ■, oxonic acid; Δ, control]
Figure 1B:
Figure 1C:
Figure 1D:
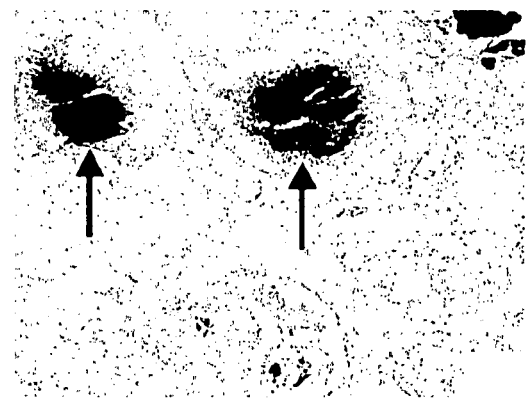

This invention relates to a method of treating hypertension comprising administering a therapeutically effective amount of an agent capable of reducing uric acid levels in a patient in need of such treatment. A reduction in uric acid levels would reduce the risk of hypertension, coronary heart disease, renal dysfunction, cardiovascular morbidity and mortality. Current standards for elevated uric acid levels are 7 mg/dl. However, patients with uric acid levels of 10 mg/dl are a high risk for the above-noted cardiovascular conditions, between 6 and 10 mg/dl are at an increased risk for the above-noted cardiovascular conditions, or a reduced risk with uric acid levels of >4 and <6 mg/dl.

A method of preventing hypertension comprising administering a therapeutically effective amount of an agent capable of reducing uric acid levels in a patient in need of such treatment.

A method of treating coronary heart disease comprising administering a therapeutically effective amount of an agent capable of reducing uric acid levels in a patient in need of such treatment.

A method of treating and preventing eclampsia comprising administering a therapeutically effective amount of an agent capable of reducing uric acid levels in a patient in need of such treatment.

An agent capable of reducing uric acid levels by about 0.2 mg /dl. The agent capable of reducing uric acid levels, which is selected from the group consisting of: gene therapy, a xanthine oxidase inhibitor; a uricosuric agent; supplements of the uricase protein and a urate channel inhibitor, or combinations of these agents. Specific examples of agents that are capable of reducing uric acid levels include but are not limited to:

a gene therapy such as one that targets the overexpression of uricase, the enzyme responsible for the breakdown of uric acid to allantoin;

a xanthine oxidase inhibitor, such as allopurinol, and carprofen;

a uricosuric agent, which is defined as an inhibitor of the organic anion transport channels and/or voltage sensitive transport channels acting in the kidney, such agents include but are not limited to: losartan, benzbromaraone, benziodarone, probenecid, sulfinpyrazone ethebencid, orotic acid, ticrynafen and zoxazolamine;

a supplement of the uricase protein which might be delivered as a conjugate with polyethylene glycol or another delivery system; and a urate channel inhibitor, is a means for interfering with the uric acid transport mechanism by blocking the influx of uric acid into cells.

A pharmaceutical composition comprising a renin angiotensin system (RAS) inhibitor or a pharmaceutically acceptable salt thereof and the agent capable of reducing uric acid levels or a pharmaceutically acceptable salt thereof as recited above and a pharmaceutical carrier. The renin angiotensin system inhibitor, such as an angiotensin converting enzyme inhibitor, an angiotensin II antagonist or a renin inhibitor. Representative RAS inihibitors include: captopril, cilazapril, enalapril, fosinopril, lisinopril, quinapril, ramapril, zofenopril, candesartan cilexetil, eprosartan, irbesartan, losartan, tasosartan, telmisartan, and valsartan, or pharmaceutically acceptable salts thereof. Also within the scope of this invention is the combination of an agent capable of reducing uric acid levels with a combination RAS inhibitor with a diuretic, such as hydrochlorothiazide, furosemide, etc. Specific examples, include but are not limited to the above RAS inhibitors with hydrochlorothiazide.

A combination therapy comprising the administration, concomitantly, simultaneously or sequentially, of therapeutically effective amounts of a RAS inhibitor and the agent capable of reducing uric acid levels as recited above. Also within the scope of this invention is the combination therapy as recited above that includes an agent capable of reducing uric acid levels with a combination RAS inhibitor with a diuretic, such as hydrochlorothiazide, furosemide, etc. Specific examples, include but are not limited to the above RAS inhibitors with hydrochlorothiazide.

Also within the scope of the invention is a pharmaceutical composition comprising an agent which stimulates nitric oxide production via endothelial and/or neuronal nitric oxide synthase or a pharmaceutically acceptable salt thereof and the agent capable of reducing uric acid levels or a pharmaceutically acceptable salt thereof as recited above and a pharmaceutical carrier. An agent which stimulates nitric oxide production via endothelial and/or neuronal nitric oxide including, but not limited to L-Arginine, nitrates and nitrate-mimetics and gene therapy, such as one that targets the overexpression endothelial and/or neuronal nitric oxide synthase.

The studies were performed on rats in which the serum uric acid was raised to a mild (1.5 to 2.0-fold) degree, using an enzyme inhibitor of uricase, an enzyme involved in the degradation of uric acid. Rats made mildly hyperuricemic developed significant hypertension within a few weeks, and this was associated with stimulation of renin (documented by renin staining in the kidney) and by a fall in neuronal NOS in the macula densa (a tubular segment in the kidney involved in regulation of renal blood flow) and of endothelial cell NOS. Associated with these findings was the development of renal fibrosis with increased collagen deposition and macrophage infiltration. These changes could be prevented by lowering the uric acid with allopurinol.

The studies provide a mechanism for the long-observed association of uric acid with hypertension, cardiovascular disease and renal disease, and for the first time provides direct experimental evidence that uric acid is causal rather than simply a marker for associated cardiovascular risk factors. It thus provides the first direct rationale for lowering uric acid as a means for not only preventing the development of hypertension but also for its treatment—a substantial finding given that 25% of the worlds population will become hypertensive. It is also relevant to a number of other diseases, including eclampsia (a disease afflicting pregnant women associated with hypertension, renal disease and an elevated uric acid but in which the latter was thought only to be a marker), to cyclosporine nephropathy (one of the complications of transplantation in which hypertension, renal disease and an elevated uric acid are central features), to progressive renal disease, and even to aging associated hypertension and renal disease. The observation that blacks have higher uric acid levels also provides a mechanism to explain the reason they are more susceptible to hypertension.

The studies show that increasing the uric acid level in the rat will cause hypertension and renal disease, and that lowering it will lower the blood pressure and prevent the development of renal disease. So far we have used pharmacologic agents for this purpose—such as the use of allopurinol, losartan, or benziodarone. However, there are numerous other possible ways to lower uric acid—these could include repleting humans with uricase (the enzyme that degrades uric acid to allantoin). Unlike most mammals, man had a series of mutations of the uricase gene early in his evolution—we have hypothesized that during this period, when man was on a very low salt diet, that the increase in uric acid would have helped maintain blood pressure under those conditions. Indeed, this was confirmed by our experimental studies in the rat. However, it may be now prudent to replace uricase in man as a means for preventing the development of hypertension—this could be done by gene therapy or by supplying the uricase protein, such as by conjugation with polyethylene glycol or other method. Future therapies might also be directed at blocking the influx of uric acid into cells by interfering with the uric acid transport mechanism.

The instant invention provides direct evidence that mild hyperuricemia in rats induces hypertension, as well as subtle renal injury and fibrosis, through a crystal-independent mechanism mediated by activation of the renin angiotensin system and downregulation of neuronal nitric oxide synthase in the macula densa. This observation may explain why hyperuricemia has been found to predict the development of hypertension [Selby, J. V., Friedman, G. D., and Quesenberry, C. P., Precursors of essential hypertension: pulmonary function, heart rate, uric acid, serum cholesterol, and other serum chemistries. *Am J Epidemiol* 131:1017-27 (1990), Jossa, F., et al., Serum uric acid and hypertension: the Olivetti heart study. *J Hum Hypertens* 8:677-681 (1994), and Goldstein, H. S., and Manowitz, P., Relationship between serum uric acid and blood pressure in adolescents. *Annals Hum Biol* 20:423-431 (1993)], and may also be relevant to the 25 to 50% of the hypertensive population who are found to be hyperuricemic at presentation [Cannon, P. J., Stason, W. B., Demartini, F. E., Sommers, S. C., and Laragh, J. H., Hyperuricemia in primary and renal hypertension. *N Engl J Med* 275:457-464 (1966)]. These studies may also provide a mechanism to explain how hyperuricemia can thwart the beneficial effects of diuretics on overall cardiovascular mortality [Franse, L. V., Pahor, M., and Barli, M. D., Serum uric acid, it's change with diuretic use and risk of cardiovascular events in the Systolic Hypertension in the Elderly Program (SHEP). *American Society of Hypertension Annual Meeting*, May 1999, New York.]. Furthermore, the finding that hyperuricemia can induce renal fibrosis may provide a mechanism for the development of 'gouty nephropathy' [Talbott, J. H., and Terplan, K. L., The kidney in gout *Medicine* 39:405-50, 1960, and Gonick, H. C., Rubini, M. E., Gleason, I. O., and Sommers, S. C., The renal lesion in gout. *Annals Int Med* 62:667-674, 1968], as it has been hard to attribute the diffuse injury to urate crystal deposition alone [Beck, L. H., Requiem for gouty nephropathy *Kidney Int* 30:280-287 (1986), and Nickeleit, V., and Mihatsch, M. J., Uric acid nephropathy and end-stage renal disease-Review of a nondisease. *Nephrol Dial Transpl* 12:1832-1838 (1997)]. It also suggests a true pathogenic role for uric acid in familial hyperuricemic nephropathy, an inherited disorder in which hyperuricemia, renal vasoconstriction, hypertension and interstitial renal disease develop [McBride, M. B., Simmonds, H. A., Moro, F. Familial renal disease or familial juvenile hyperuricaemic nephropathy? *J Inher Metab Dis* 20:351-353 (1997)]. The documentation that an elevated uric acid causes hypertension also helps resolve the clinical and epidemiological controversies surrounding the role of uric acid in cardiovascular disease, as multivariate analyses would not be expected to show uric acid to be an independent risk factor when controlled for variables to which it is causally linked [Johnson, R. J., and Tuttle, K., Much ado about nothing, or much to do about something: The continuing controversy on the role of uric acid in cardiovascular disease. *Hypertension* 35:E10-E10 (2000)].

While the data suggests that an elevated uric acid can increase blood pressure and induce renal disease through a mechanism that involves activation of the renin angiotensin system and inhibition of neuronal nitric oxide synthase, it is important to recognize that there may be additional mechanisms by which uric acid contributes to cardiovascular disease. Indeed, there are other studies have shown that uric acid remains an independent cardiovascular risk factor even after controlling for hypertension and renal disease [Fang, J., and Alderman, M. H., Serum uric acid and cardiovascular mortality. The NHANES I Epidemiologic Follow-up Study, 1971-1992 *JAMA* 283:2404-2410 (2000), Bengtsson, C., Lapidus, L., Stendahl, C., and Waldenström, J., Hyperuricemia and risk of cardiovasular disease and overall death. *Acta Med Scand* 224:549-55 (1988), and Alderman, M. H., Cohen, H., Madhavan, S., and Kivlighn, S., Serum uric acid and cardiovascular events in successfully treated hypertensive patients. *Hypertension* 34:144-150 (1999)].

Finally, the observation that inhibition of uricase can prevent the fall of blood pressure under low salt conditions provides a mechanism to explain why the mutations of the uricase gene, giving rise to an elevated uric acid, were preferentially conserved during early primate development. Indeed, studies had suggested that humans were on a very low sodium diet (20-40 mmol/day of sodium) for the great majority (99.8%) of the last 3.5 million years, and it is only in the last several thousand years that man has been on the modem day, high salt diet [Eaton, S. B., and Konner, M., Paleolithic nutrition: A consideration of its nature and current implications. *N Engl J Med* 312: 283-289 (1985)]. It is also of interest that studies of primitive societies have documented a low prevalence of hypertension and cardiovascular disease [Young, D. B., Lin, H., and McCabe, R. D., Potassium's cardioprotective mechanisms. *Am J Physiol* 268:R825-R837 (1995), and Tobian, L. Salt and hypertension. Lessons from animal models that relate to human hypertension. *Hypertension* 17[suppl I]:I52-I58 (1991)], suggesting that the current 'epidemic' of cardiovascular disease and hypertension may be a consequence of modem society. While this mutation may have benefited early humans, it is hypothesized that in modern societies it plays a critical role in the pathogenesis of hypertension and cardiovascular disease.

A major complication of chronic cyclosporine treatment is CSA nephropathy [Myers, B. D., Newton, L., Cyclosporine induced chronic nephropathy: an obbliterative microvascular renal injury. *J Am Soc Nephrol* 1991; 2: S45, and Myers, B., Cyclosporine nephrotoxicity, *Kidney Int* 1986; 30:964.], which is characterized by arteriolar hyalinosis and tubulointerstitial disease. The pathogenesis is considered to be secondary to intense renal vasoconstriction induced by angiotensin II and other vasoactive substances [Bennett, W. M., De Mattos, A., Meyer, M. M., Andoh, T. F., and Barry, J. M., Chronic cyclosporine nephropathy. The Achille's heel of immunossupressive therapy. *Kidney Int* 1996; 50:1089, Myers, B., Cyclosporine nephrotoxicity. *Kidney Int* 1986; 30:964, and Bennett, W. M., Burdmann, E. A., Andoh, T. F., Houghton, D. C., Lindsley, J., and Elzinga, L. W., Nephrotoxicity of immunossupressive drugs. *Nephrol Dial Transplant* 1994; 9:141, and Burdmann, E. A., Andoh, T. F., and Nast, C. C., et al., Prevention of experimental cyclosporine induced interstitial fibrosis by losartan and enalapril. *Am J Physiol* 1995; 269: F491.].

Cyclosporine use is also associated with the development of hyperuricemia, secondary to a decrease in uric acid excretion [Hoyer, P. F., Lee, I. K., Oemar, B. S., Krohn, H. P., Offner, G., and Brodlel, J., Renal handling of uric acid under cyclosporine A treatment. *Pediatr Nephrol* 1988; 2:18, Cohen, S. L., Boner, G., Rosenfeld, J. B., et al., The mechanism of hyperuricaemia in cyclosporine-treated renal transplant recipients. *Transplant Proc* 1987; 19:1829, and Noordzij, T. C., Leunissen, K. L. M., and Van Hoff, J. P., Renal handling of urate and the incidence of gouty arthritis during cyclosporine and diuretic use. *Transplantation* 1991; 52(1): 64.]. While the risk of hyperuricemia in patients on CSA has generally been considered only to be gout [West, C., Carpenter, B. J., and Hakala, T. R., The incidence of gout in renal transplant recipients. *Am J Kidney Dis* 1987; 10: 369.], it is of interest that there has been a longstanding controversy on the role of hyperuricemia in mediating tubulointerstitial diseases. Numerous studies have documented that patients with gout have a high prevalence of tubulointerstitial disease ("gouty nephropathy") [Beck, L. H., Requiem for gouty nephropathy. *Kidney Int* 30:280-287, 1986, Emmerson, B. T., and Row, P. G., An evaluation of the pathogenesis of the gout kidney. *Kidney Int*. 1975; 8:65, Gonick, H. C., Rubini, M. D., Gleason, I. O., and Sommers, S. C. The renal lesion in gout. *Ann Int Med* 1965; 62:667, and Talbot, J. H., and Terplan, K. L., The kidney in gout. *Medicine* 1960; 39:405. Steele T H: Hyperuricemic nephropathies. *Nephron* 1999; 81 (1 suppl 1): 45.] and these patients also have evidence for intense renal vasoconstriction [Messerli, F. H., Frolich, E. D., Drelinski, G. R., Suarez, D. H., and Aristimuno, G. G., Serum uric acid in essential hypertension: an indicator of renal vascular involvement. *Ann Int Med* 1980; 93:817.]. However, it has remained controversial as to whether the hyperuricemia per se contributes to the renal disease or whether the renal disease results from other associated risk factors such as hypertension [Nickeleit, V., and Mihatsh, M. J., Uric acid nephropathy and end-stage renal disease. Review of a non-disease. *Nephrol Dial Transplant* 1997; 12: 1832.]. In this study we have addressed the role of uric acid in a model of CSA nephropathy in rats and examined the hypothesis that hyperuricemia may significantly augment cyclosporine mediated renal injury.

The first finding was that CSA, independent of oxonic acid, was associated with an increase in serum uric acid with a tendency for a reduction in fractional urate excretion. In rats receiving CSA and oxonic acid, the serum urate levels were higher but the fractional urate excretion remained low to normal. These findings are similar to those observed in humans [Hoyer, P. F., Lee, I. K., Oemar, B. S., Krohn, H. P., Offner, G., and Brodhel, J., Renal handling of uric acid under cyclosporine A treatment. *Pediatr Nephrol* 1988; 2:18, and Cohen, S. L., Boner, G., Rosenfeld, J. B., et al., The mechanism of hyperuricaemia in cyclosporine-treated renal transplant recipients. *Transplant Proc* 1987; 19:1829.] and document the clinical relevance of this model.

The second important finding of this study was that hyperuricemia significantly exacerbated the tubulointerstitial disease and arteriolar hyalinosis induced by cyclosporine. Parameters analyzed included osteopontin, which is a sensitive marker of tubulointerstitial injury, interstitial and glomerular macrophage accumulation and interstitial deposition of type III collagen. Interestingly, all of these parameters were significantly worse in rats treated with CSA and OA compared to rats treated with CSA alone.

The mechanism by which hyperuricemia exacerbates renal disease is of intense interest. An important finding in our study is that it does not involve intrarenal crystal deposition. Utilizing different stains for uric acid we were unable to identify crystals in these lesions. Furthermore, the pattern of tissue injury was more consistent with an "ischemic" pattern [Duncan, H., and Dixon, A. S., Gout, familial hyperuricemia and renal disease. *Q J Med* 1960; 29: 127.] as opposed to an "obstructive" pattern as seen with crystal induced intratubular deposition [Waisman, J., Mwasi, L. M., Bluestone, R., and Klinemberg, J. R., Acute hyperuricemic nephropathy in rats. An electron microscopy study. *Am J Pathol* 1975; 81(2): 367, and Tykarski, A., Evaluation of renal handling of uric acid in essential hypertension: hyperuricemia related to decreased urate secretion. *Nephron* 1991; 59:364.]. In addition the ability of CSA to reduce the fractional excretion of urate resulted in urinary levels lower than that associated with the acute urate nephropathy model, in which urinary urate excretion is typically increased [Bluestone, J., Waisman, J., and Klinemberg, J. R., Chronic experimental hyperuricemia nephropathy. Biochemical and morphological characterization. *Lab Invest* 1975; 33(3): 273.].

Therefore, it is our contention that hyperuricemia may augment renal injury in this model by potentiating CSA-mediated renal vasoconstriction. Furthermore, gout is associated with both tubulointerstitial disease and renal vasoconstriction. It is of interest that familial hyperuricemic nephropathy is characterized by reduced fractional urate excretion, renal vasoconstriction and tubulointerstitial disease in which intrarenal urate crystal deposition is often absent [Mateos, F. A., and Puig, J. C., Renal hemodynamics in familial nephropathy associated with hyperuricemia. *Adv Exp Med Biol* 1991; 309: 301, and Simmonds, H. A., Warren, D. J., Cameron, J. S., Potter, C. F., and Farebrother, D. A., Familial gout and renal failure in young women. *Clin Nephrol* 1980; 14:176.].

The presence of hyperuricemia in rats with CSA-induced nephropathy is associated with significantly worse tubulointerstitial renal injury, but does not involve intrarenal crystal deposition. This finding has significant implications not only in our understanding of the pathogenesis of CSA nephropathy, but also in the role of hyperuricemia in the progression of renal disease.

The following examples illustrate this method of treatment/prevention, and as such are not to be considered as limiting the invention set forth in the claims appended hereto.

EXAMPLES

Experimental Design

All studies utilized adult male Sprague-Dawley rats (Simonsen Laboratories, Gilroy Calif.)(200-250 g).

Example 1

Rats were placed on a normal salt (NaCl 0.26%) diet with or without 2% oxonic acid (Ziegler Bros, Gardners, Pa.) added to the diet and rats were sacrificed at week 7.

Systolic blood pressure was measured by tail cuff sphyngomanometer using an automated system with photoelectric sensor (IITC, Life Science) that has been shown to closely correlate with intra-arterial blood pressure measurements [Fischer E, Schnermann, J., Briggs, J. P, Kriz, W. Ronco, P. M., Bachmann, S. Ontogeny of NO synthase and renin in juxtaglomerular apparatus of rat kidneys. Am J Physiol 268: F1164-76, 1995].

Example 2

Rats were placed on a low sodium diet (NaCl, 0.125%) with or without 2% oxonic acid for 7 weeks. A third group were administered allopurinol in the drinking water (150 mg/L) with weekly adjustments of the dose depending on the uric acid level.

Systolic blood pressure was measured by tail cuff sphyngomanometer using an automated system with photoelectric sensor (IITC, Life Science) that has been shown to closely correlate with intra-arterial blood pressure measurements [Fischer E, Schnermann, J., Briggs, J. P, Kriz, W. Ronco, P. M., and Bachmann, S., Ontogeny of NO synthase and renin in juxtaglomerular apparatus of rat kidneys. Am J Physiol 268: F1164-76, 1995].

Example 3

Rats were placed on the low sodium diet with oxonic acid for 7 weeks, and then were matched based on uric acid level and blood pressure in various groups to either receive allopurinol, have the oxonic acid withdrawn from the diet, or continue the oxonic acid/low salt diet. A control group of six rats were placed on the lowsodium diet alone for 11 weeks. All of these rats were sacrificed at week 11.

Systolic blood pressure was measured by tail cuff sphyngomanometer using an automated system with photoelectric sensor (IITC, Life Science) that has been shown to closely correlate with intra-arterial blood pressure measurements [Fischer, E., Schnermann, J., Briggs, J. P, Kriz, W., Ronco, P. M., and Bachmann, S., Ontogeny of NO synthase and renin in juxtaglomerular apparatus of rat kidneys. *Am J Physiol* 268: F1 164-76, 1995].

Example 4

Rats were placed on either low salt diet, low salt diet with 2% oxonic acid, low salt diet with oxonic acid and enalapril (1 mg/kg/d in drinking water), or low salt diet with oxonic acid and L-Arginine (1% in drinking water).

Systolic blood pressure was measured by tail cuff sphyngomanometer using an automated system with photoelectric sensor (IITC, Life Science) that has been shown to closely correlate with intra-arterial blood pressure measurements [Fischer, E., Schnermann, J., Briggs, J. P., Kriz, W., Ronco, P. M., and Bachmann, S., Ontogeny of NO synthase and renin in juxtaglomerular apparatus of rat kidneys. *Am J Physiol* 268: F1 164-76, 1995].

Functional Data:

Serum and urine uric acid were measured by a carbonate phosphotungstate method [Henry, R. J., Sobel, C., and Kim, J., A modified carbonate phosphotungstate method for the determination of uric acid and comparison with the spectophotometric uricase method. *Am J Clin Pathol* 1957; 28:152.]. Serum blood urea nitrogen was measured by a standard kit (Sigma, St Louis, Mo.).

Renal Immunohistochemistry:

Renal biopsies were fixed in Methyl-Carnoy's, 10% formalin or 100% ethanol and embedded in paraffin. The presence of uric acid crystals was evaluated by staining 4-µm ethanol-fixed sections with de Galantha and modified Von Kossa stains. Kidney tissue from rats with acute uric acid nephropathy, induced with oxonic acid and uric acid administration was used as a positive control [Stavric, B., Johnson, W. J., and Grice, H. C., Uric acid nephropathy: An experimental model, *Proc. Soc. Exp. Biol. Med.* 130: 512-16 (1969) .]. Light microscopy was performed in 4-µm sections of Methyl-Carnoy's fixed tissue stained with periodic acid Schiff (PAS) reagent or with hematoxylin and eosin.

Methyl-Carnoy's fixed tissue sections were analyzed by indirect immunoperoxidase [Lombardi, D., Gordon, K. L., Polinsky, P., Suga, S., Schwartz, S. M., and Johnson, R. J. Salt sensitive hypertension develops after transient exposure to angiotensin II. *Hypertension* 33:1013-1019, 1999] staining with the following primary antibodies: OP199, a goat polyclonal antibody against osteopontin (OPN)(gift of C. Giachelli, Univ of Wash., Seattle); ED-1, a monoclonal antibody to rat monocytes and macrophages (Serotec); goat antihuman type III collagen (Southern Biotechnology Associates Inc, Birminghan Ala.); and anti-renin, a mouse antibody to human renin (Sanofi Recherche, Montpellier, France). Sections were incubated with a secondary antibody followed by horseradish peroxidase-conjugated avidin D (Vector Laboratories, Burlingame, Calif.), diaminobenzidine (Sigma) with or without nickel chloride as a chromogen, and counterstained with methyl green.

NOS1 was detected on formalin fixed tissue sections with a rabbit anti-rat neuronal nitric oxide synthase (Transduction Laboratories, Lexington, Ky.), followed by a biotinylated secondary antibody, diaminobenzidine with nickel chloride and counterstained with nuclear fast red.

Quantification of Morphologic Data:

All quantification was performed blinded. The tubular expression of osteopontin (OPN), which is a sensitive marker of tubulointerstitial injury, was calculated as the percent of renal cortex occupied by OPN-positive tubules [Lombardi, D., Gordon, K. L., Polinsky, P., Suga, S., Schwartz, S. M., and Johnson, R. J. Salt sensitive hypertension develops after transient exposure to angiotensin II. *Hypertension* 33:1013-1019, 1999]. Utilizing computer-assisted image analysis software (Optimas V6.2, Media Cybernetics, Silver Springs, Md.) and digitized images, the percent of area occupied by OPN positive tubules per 4 mm$^2$ field at a magnification of 50× was measured and the mean percent area calculated for each biopsy. The interstitial deposition of collagen type III was calculated as the % of renal cortex occupied by collagen III, noted by immunostaining, by computer image analysis. The mean number of interstitial macrophages (ED-1+cells) in each biopsy was calculated in a blinded manner by counting the total number of positive interstitial cortical cells in 20 sequentially selected 0.25 mm$^2$ grids at 200× magnification. Renin expression was quantified by the number of glomeruli with positive staining for juxtaglomerular renin using a minimum of 100 glomeruli in each biopsy as previously described [Eng, E., et al., Renal proliferation and phenotypic changes in rats with two-kidney, one-clip Goldblatt hypertension. *Am J Hypertens* 7:177-185 (1994)]; this has been shown previously to correlate with intrarenal renin content[Eng, E., et al., Renal proliferation and phenotypic changes in rats with two-kidney, one-clip Goldblatt hypertension. *Am J Hypertens* 7:177-185 (1994)]. NOS1 was quantified by a blinded counting of the number of positive macula densa cells staining with anti-NOS1 antibody using a minimum of 100 glomeruli per biopsy [Eng, E., et al., Renal proliferation and phenotypic changes in rats with two-kidney, one-clip Goldblatt hypertension. *Am J Hypertens* 7:177-185 (1994)]. Previous studies have shown that the number of NOS1 cells correlates with intrarenal NOS1 activity [Fischer, E., Schnermann, J., Briggs, J. P, Kriz, W., Ronco, P. M., and Bachmann, S., Ontogeny of NO synthase and renin in juxtaglomerular apparatus of rat kidneys. *Am J Physiol* 268:F1 164-76, 1995].

Statistical Analysis

All values are expressed as mean±standard error, unless otherwise stated. Statistical significance (p<0.05) was evaluated by ANOVA and unpaired Student's t test with appropriate correction for multiple comparisons.

An Animal Model of Mild Hyperuricemia

An animal model of mild hyperuricemia was developed using the rat. Several previous groups had reported that hyperuricemia could be induced in rats by feeding them oxonic acid, which is a uricase inhibitor [Stavric, B., Johnson, W. J., and Grice, H. C., Uric acid nephropathy: An experimental model, *Proc Soc Exp Biol Med* 130:512-16 (1969)]. In most studies uric acid supplements were also added to the diet. Unfortunately, this model usually results in a six to ten-fold increase in serum uric acid levels with marked uricosuria, resulting in acute renal failure from obstruction of the renal tubules with urate crystals [Stavric, B., Johnson, W. J., and Grice, H. C., Uric acid nephropathy: An experimental model, *Proc Soc Exp Biol Med* 130:512-16 (1969)]. Likewise, targeted deletion of the uricase gene in mice also results in marked hyperuricemia, intrarenal urate crystal deposition, and renal failure [Bradley, A., and Caskey, C. T., Hyperuricemia and urate nephropathy in urate oxidase deficient mice. *Proc Natl Acad Sci USA* 91:742-746 (1994)]. While these latter models mimic the acute urate nephropathy syndrome observed in occasional patients with cancers following chemotherapy ('tumor lysis syndrome') [Robinson, R. R., and Yarger, W. E., Acute uric acid nephropathy *Arch Int Med* 17:839-840 (1977)], they are inappropriate models for the mild hyperuricemia observed in patients with cardiovascular disease.

Hyperuricemia was induced in rats by feeding 2% oxonic acid in the diet, resulting in a mild increase in the serum uric acid level. Although urinary uric acid increased two-fold, it was not at a level sufficient to cause intrarenal crystal deposition (FIG. 1). Routine light microscopy of the kidney revealed normal histology at 7 weeks, and special stains for uric acid crystals were negative (FIG. 1). Rats administered the oxonic diet also appeared completely healthy, although the body weight at the end of the study (7 weeks) was slightly lower in the hyperuricemic animals (367.6±17 vs. 394±18 g body weight, oxonic acid diet vs. control, p<0.05).

Hyperuricemia Induces Blood Pressure Elevation

Figure 2:
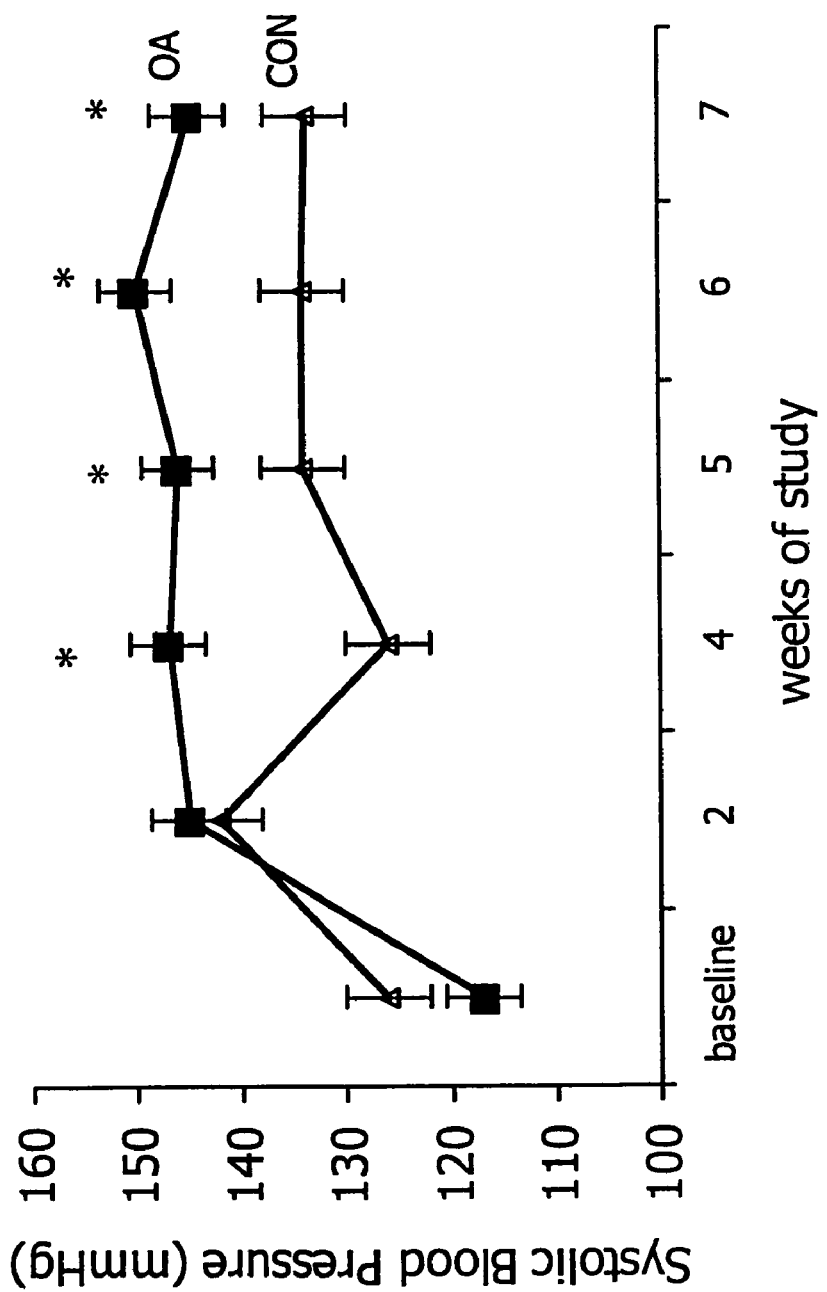
FIG. 2—Hyperuricemia Elevates Blood Pressure in Rats. Rats placed on oxonic acid (2%) develop a modest elevation of blood pressure after 3 weeks on a normal sodium (0.26% NaCl) diet. $*p<0.05$ versus control. [Key: ■, oxonic acid; Δ, control]
Figure 3A:
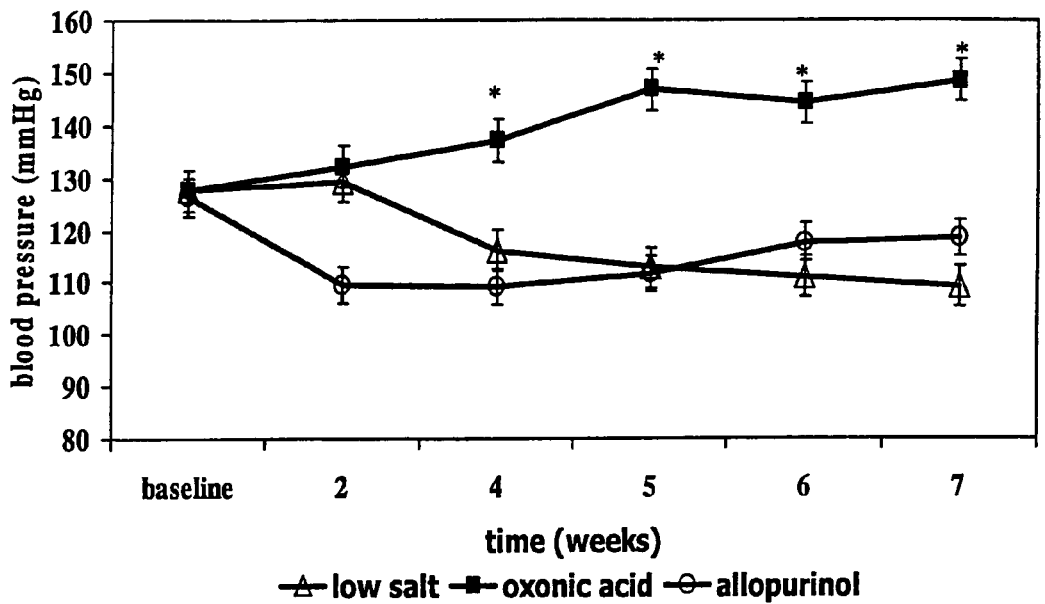
FIG. 3A shows the blood pressures.
Figure 3B:
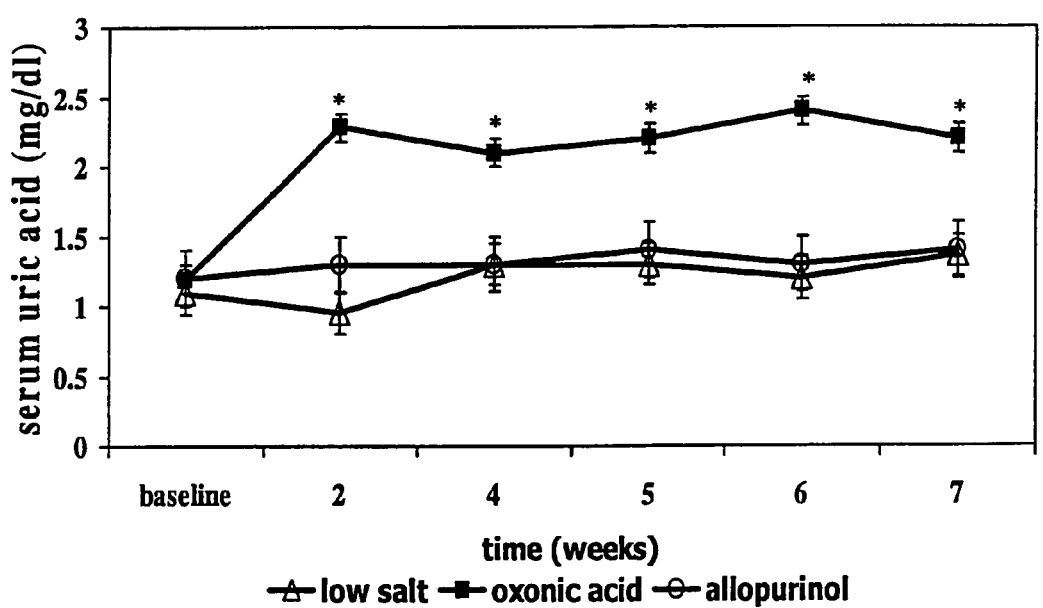
FIG. 3B shows the uric acid levels. [Key: ■, oxonic acid; Δ, control; ○, allopurinol+oxonic acid] $*p<0.05$ versus control, $\dagger p<0.05$ vs. oxonic acid alone.
Figure 4:
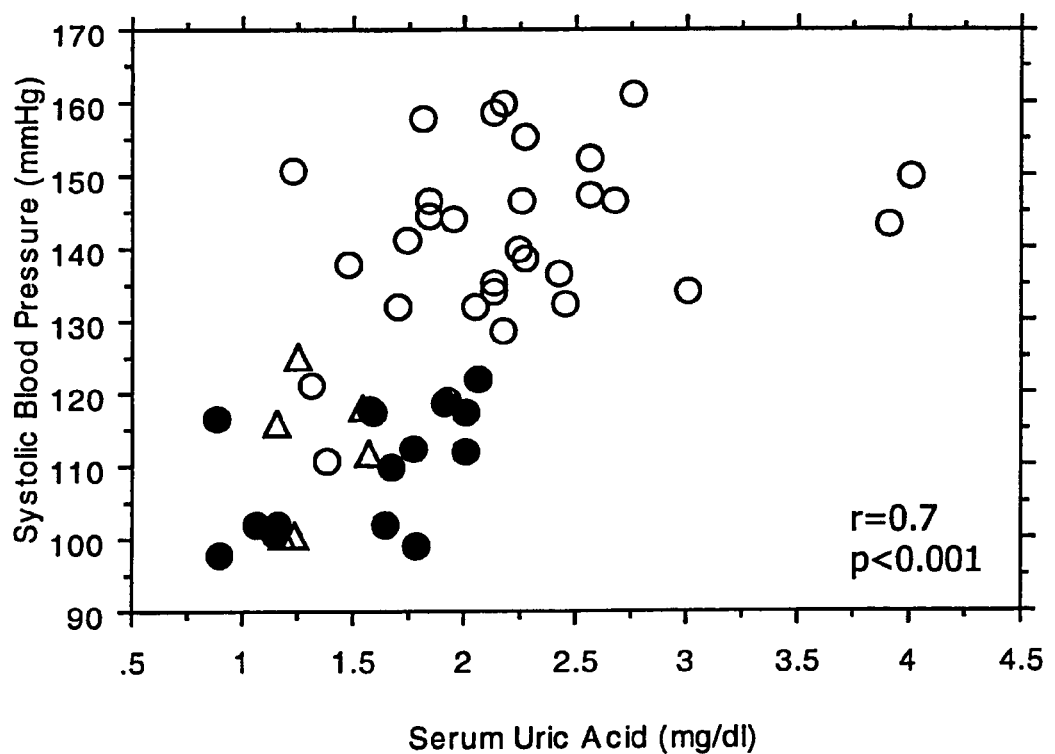
FIG. 4—Hyperuricemia Correlates with Blood Pressure. Shown are the serum uric acid levels in individual rats on a low salt diet (closed circles), low salt+oxonic acid (open circles) and on a low salt diet+oxonic acid+allopurinol (triangles) at 7 weeks with the corresponding systolic blood pressures. A strong correlation is present ($r=0.7$, $n=52$, $p<0.001$).

A remarkable finding was that rats with hyperuricemia developed increased blood pressure within 4 weeks after commencing the diet (FIG. 2). Systolic blood pressures averaged 10 to 30 mm Hg higher in the hyperuricemic rats compared to controls. The observation that an elevated uric acid induced an increase in blood pressure, suggests that it might act to help maintain blood pressure in conditions associated with a low salt intake, such as occurred during early hominoid evolution [Eaton, S. B., and Konner, M., Paleolithic nutrition: A consideration of its nature and current implications. *N Engl J Med* 312: 283-289 (1985)]. As shown in FIG. 3, control rats placed on a modest sodium restricted diet had a fall in blood pressure within 3 weeks. In contrast, hyperuricemic rats on a low salt diet showed a significant increase in blood pressure resulting in 30 to 40 mmHg differences between groups. Blood pressures showed a direct correlation with uric acid levels in both experiments (n=52, r=0.7, p<0.0001 for the low salt study; n=12, r=0.7, p<0.0001 for the normal salt study) (FIG. 4). An increase of 0.5 mg/dl in uric acid resulted in an increase in systolic blood pressure of 20 mm Hg (FIG. 4). At uric acid levels of 2 mg/dl or higher (corresponding to a 50% increase in uric acid over baseline) blood pressures were in the hypertensive range (systolic blood pressure>140 mm Hg). Interestingly, rats on an oxonic acid diet that did not develop hyperuricemia did not have elevated blood pressures (FIG. 4).

Figure 5A:
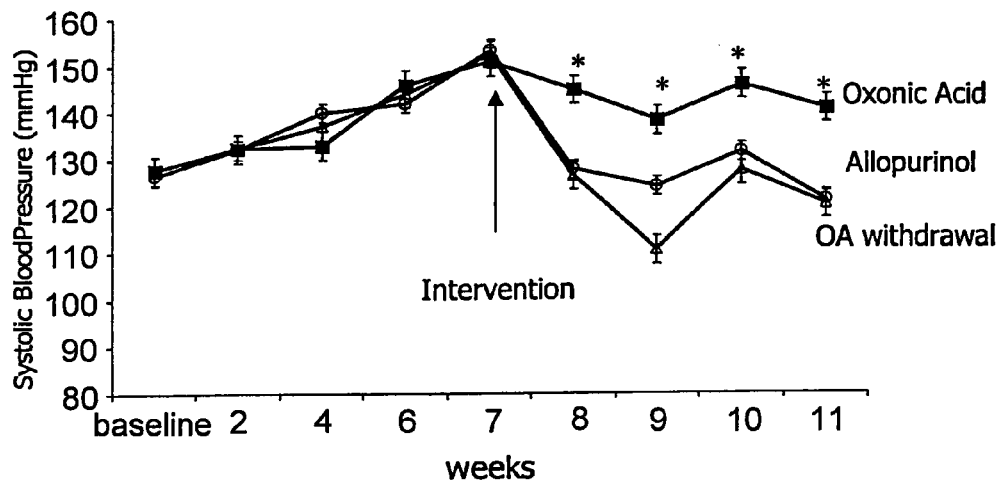
FIG. 5A shows the blood pressures, and FIG. 5B shows the uric acid levels. [Key: ■, oxonic acid; ∆, oxonic acid withdrawal; ○, allopurinol+oxonic acid].

To document that the elevation in blood pressure was due to the hyperuricemia and not a nonspecific effect of the oxonic acid, hyperuricemic rats were co-administered the xanthine oxidase inhibitor, allopurinol, with the oxonic acid. Allopurinol administered from the initiation of the oxonic acid diet prevented the development of hyperuricemia and hypertension (FIG. 3A and B). Furthermore, in hypertensive, hyperuricemic rats, either withdrawal of the oxonic acid or adding allopurinol also resulted in a reduction in the blood pressure in association with a fall in serum uric acid values (FIGS. 5A and B).

Mild Hyperuricemia Causes Renal Fibrosis

In an attempt to understand the mechanism for the hypertensive effect of hyperuricemia, we carefully examined the kidneys of the hyperuricemic and control animals. At 7 weeks both routine light microscopy (FIG. 1) and blood urea nitrogen levels were normal in the hyperuricemic rats. However, special immunohistochemical stains showed a striped pattern of early interstitial fibrosis, with increased deposition of interstitial collagen, macrophage accumulation, and with tubular expression of osteopontin, which is a sensitive marker of tubular injury [Lombardi, D., Gordon, K. L., Polinsky, P., Suga, S., Schwartz, S. M., and Johnson, R. J., Salt sensitive hypertension develops after transient exposure to angiotensin II. *Hypertension* 33:1013-1019, 1999]. The administration of allopurinol from the time the diet was initiated prevented the development of the fibrotic changes (Table 1).

Figure 5B:
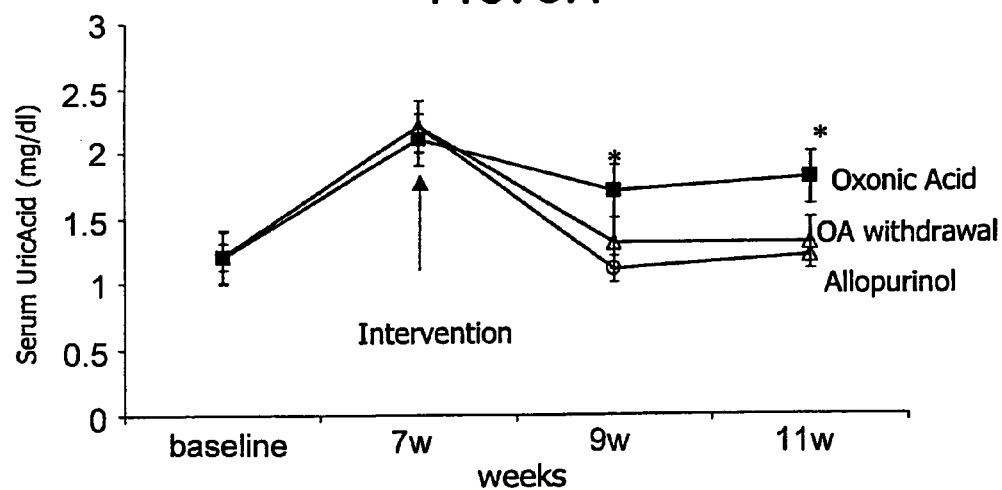
FIG. 5—Effect of Allopurinol Intervention or Oxonic Acid Withdrawal on Blood Pressure in Hyperuricemic Rats. Rats were placed on low salt diet plus oxonic acid (2%) for 7 weeks and then matched on basis of uric acid level and blood pressure into 3 groups (Oxonic acid plus low salt diet (OA/LSD); Withdrawal of oxonic acid but continuation of the LSD (OA withdrawal); and the addition of allopurinol (150 mg/L drinking water) with continuation of the OA/LSD diet (+allopurinol).

A second study was also performed in which allopurinol was added or oxonic acid withdrawn at 7 weeks and then the rats were followed for an additional 4 weeks before they were sacrificed (FIG. 5). In this study the hyperuricemic rats showed more pronounced renal fibrosis and a statistical increase in blood urea nitrogen (Table 1)(FIG. 6). Rats in which the hyperuricemia was treated by either the addition of allopurinol or by the withdrawal of oxonic acid showed significantly less renal fibrosis and lower blood urea nitrogen levels (Table 1).

[Ollerstam, A. Pittner, J., Persson E. G., and Thorup, C., Increased blood pressure in rats after long-term inhibition of the neuronal isoform of nitric oxide synthase. *J Clin Invest* 99:2212-2218, 1997.]. As with renin, the decrease in NOS-1 positive cells was largely prevented by allopurinol treatment (Table 2).

Figure 8:
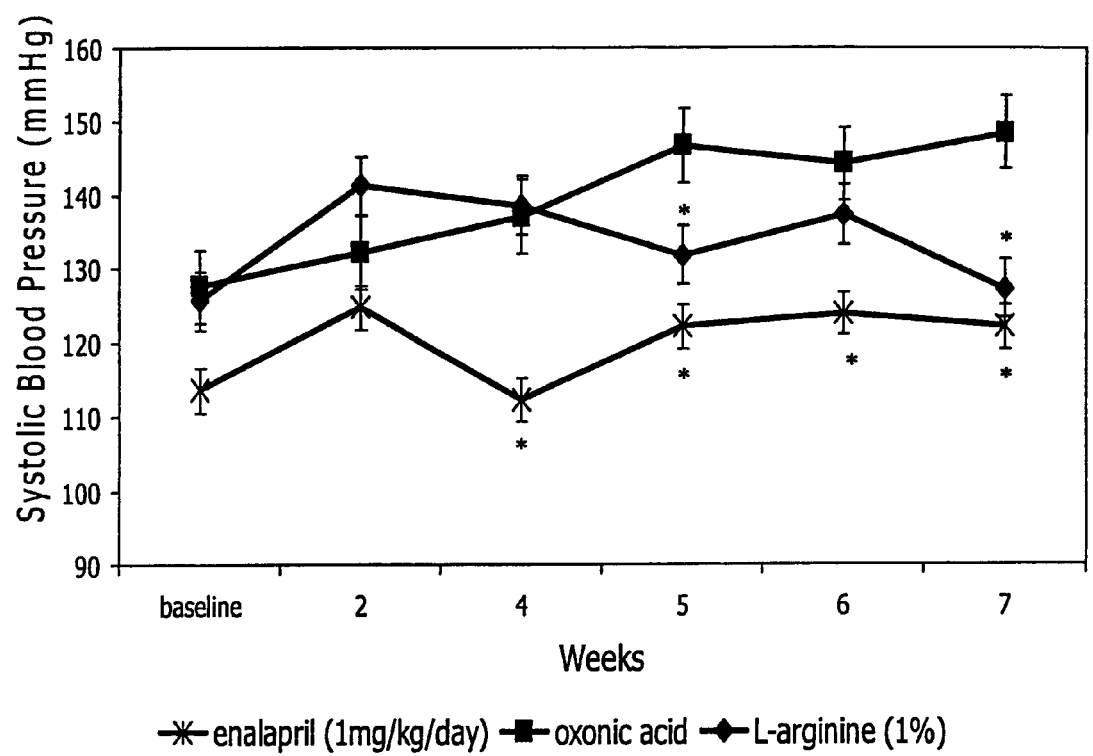
FIG. 8—The Elevated BP in Hyperuricemic Rats is Prevented by Treatment with an ACE inhibitor or with L-Arginine. Rats placed on a low salt diet with oxonic acid develop an elevated blood pressure (OA/LSD), which is prevented if enalapril (1 mg/kg/d) or L-Arginine (1%) is added to the drinking water. *p<0.05 versus OA/LSD. [Key: ■, oxonic acid; ♦, L-arginine ; *, enalapril].

To further document a role for these mediators, we administered enalapril, an angiotensin converting enzyme inhibitor, or L-Arginine, which is a substrate for nitric oxide production, to the hyperuricemic rats from the outset. As shown in FIG. 8, hyperuricemic control rats have an approximately 20 mm Hg increase in systolic blood pressure over the 7 week dietary period. L-Arginine treatment largely prevented this

TABLE 1

Hyperuricemic Rats Develop Renal Injury

| | Type III collagen (%) | ED-1 (cells/mm2) | OPN (% increase) | BUN (mg/dl) |
|---|---|---|---|---|
| Example 2: Renal Findings at 7 weeks after Oxonic Acid (OA) in presence/absence of allopurinol (AP) | | | | |
| Control (LSD) | 5.4 ± 0.3 | 18.3 ± 1.3 | 0.9 ± 0.06 | 14.4 ± 1.2 |
| OA + LSD | 8.8 ± 1.5* | 27.2 ± 1.9* | 1.8 ± 0.06* | 23.2 ± 2.3 |
| OA/LSD + Allopurinol | 6.2 ± 0.6 | 20.5 ± 0.6 | 1.3 ± 0.15*† | 15.2 ± 2.3 |
| Example 3. Effect of Oxonic Acid (OA) withdrawal or addition of Allopurinol (AP) at 7 weeks on Renal Findings at 11 weeks. | | | | |
| Control (LSD) | 7.2 ± 0.6 | 27.8 ± 1.4 | 0.7 ± 0.08 | 16.6 ± 0.9 |
| OA + LSD | 13.9 ± 0.6* | 36.5 ± 1.4* | 1.33 ± 0.14* | 24.1 ± 1.7* |
| OA withdrawal | 8.9 ± 1.6*† | 33.0 ± 1.6* | 1.08 ± 0.06*† | 18.8 ± 0.8† |
| OA/LSD + Allopurinol | 9.6 ± 0.3*† | 25.2 ± 2.6† | 0.97 ± 0.03*† | 17.7 ± 0.5† |

Abbreviations: BUN, blood urea nitrogen; ED-1, macrophages; LSD, low NaCl diet (0.125%); OA, oxonic acid; TI, tubulointerstitial.
*$p < .05$ vs. control. 24.1 ± 1.7*
†$p < 0.05$ vs LSD/OA.

Figure 7:
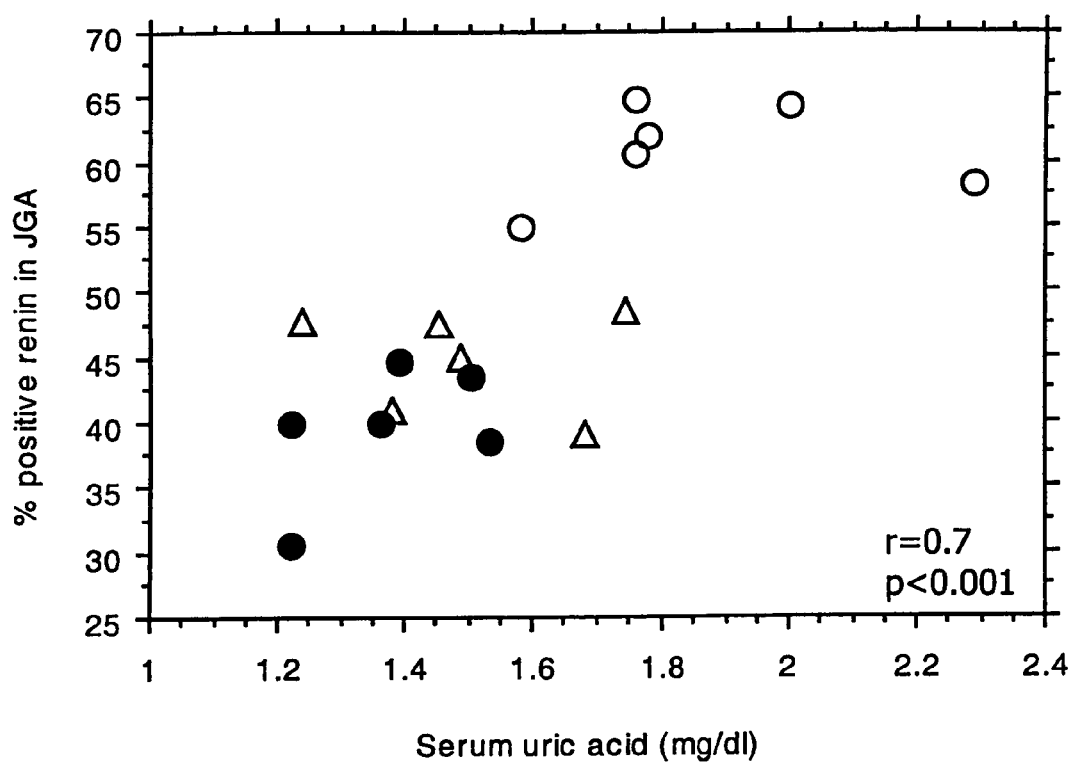
FIG. 7—Renin Correlates with Serum Uric Acid in Rats on a Low Salt Diet. There was a direct correlation between renin (measured as the % of glomeruli with juxtaglomerular renin staining) and serum uric acid levels in rats on a low sodium diet (r–0.7, n=18, p=0.0006). [Key: ○, oxonic acid; ●, low salt diet control; ∆, allopurinol+oxonic acid].

Hyperuricemia Activates the Renin Angiotensin System and Inhibits Intrarenal Neuronal Nitric Oxide Synthase The 'striped' fibrotic pattern of renal injury is characteristic of chronic vasoconstriction and/or ischemia, which is of interest given Messerli's observation that hyperuricemia in man is associated with renal vasoconstriction [Messerli,F. H., Frohlich, E. D., Dreslinski, G. R., Suarez, D. H., and Aristimuno, G. G., Serum uric acid in essential hypertension: An indicator of renal vascular involvement. *Ann Int Med* 93:817-821, 1980.]. The renal expression of two important vasoactive mediators were examined in these rats (Table 2). The percentage of glomeruli with juxtaglomerular renin staining was markedly increased in the hyperuricemic animals, a finding that correlates with increased renal renin content [Eng, E., et al., Renal proliferation and phenotypic changes in rats with two-kidney, one-clip Goldblatt hypertension. *Am J Hypertens* 7:177-185 (1994)]. There was also a direct correlation of serum uric acid levels with the percentage of renin-positive glomeruli, both in the studies using a low salt diet (r=0.7, n=18, p=0.0006, FIG. 7) and in the study using a normal salt diet (r=0.6, n=12, p=0.05). Interestingly, Saito et al., have previously reported that uric acid levels correlate with plasma renin activity in patients with essential hypertension [Saito, I., et. al. Serum uric acid and the renin-angiotensin system in hypertension. *J Am Geriatrics Soc* 26:241-247 1976.].

The effect of hyperuricemia on neuronal nitric oxide synthase (NOS1) expression in the macula densa, which is involved in regulating afferent arteriolar tone and tubuloglomerular feedback were also examined. As shown in Table 2, the number of neuronal nitric oxide synthase (NOS1) positive cells in the macula densa was decreased in hyperuricemic rats. This is particularly relevant, as chronic inhibition of NOS1 has been reported to elevate blood pressure in rats increase. Enalapril-treated hyperuricemic rats had the lowest systolic blood pressures. At 7 weeks, the systolic blood pressures in the L-Arginine and enalapril groups averaged 25 mm Hg lower than the hyperuricemic controls (p<0.05). This suggests that the hypertension and renal disease induced by hyperuricemia are dependent on both angiotensin II and the nitric oxide system.

TABLE 2

Hyperuricemia Induces Changes in Vasoactive Mediators

| | Renin (% positive JGA) | NOS-1 (positive cells/ 100 glomeruli) |
|---|---|---|
| Example 2. Renal Findings at 7 weeks after Oxonic Acid (OA) in presence/absence of Allopurinol (AP) | | |
| Control (LSD) | 39.6 ± 2.0 | 147.2 ± 12.4 |
| OA + LSD | 60.9 ± 1.5* | 80.4 ± 4.3* |
| OA/LSD + Allopurinol | 44.1 ± 1.6† | 97.4 ± 5.6* |
| Example 3. Effect of Oxonic Acid (OA) withdrawal or addition of Allopurinol (AP) at 7 weeks on Renal Findings at 11 weeks. | | |
| Control (LSD) | 41.0 ± 1.9 | 104.4 ± 11.5 |
| OA + LSD | 58.4 ± 0.8* | 65.6 ± 7.1* |
| OA withdrawal | 50.5 ± 2.1*† | 83.1 ± 10.8 |
| OA/LSD + Allopurinol | 44.2 ± 1.3† | 98.6 ± 5.1† |

Abbreviations: AP, allopurinol; glom, glomeruli; LSD, low NaCl diet (0.125%); OA, oxonic acid; MD, macula densa.
*$p < .05$ vs. control.
†$p < 0.05$ vs LSD/OA.

Example 5

Animals

Studies were conducted in 20 adult male Sprague-Dawley rats (Simmonsen Laboratories, Gilroy, Calif., USA) weighing 200 to 250 grams. All rats were fed a low salt diet (0.125% NaCl)(Zeigler Bros, Gardners, Pa.), with water ad libitum. The use of low salt diet has been shown to accelerate the development of CSA nephropathy [13,26]. In order to induce hyperuricemia, oxonic acid 2% was added to low salt diet. Because rats have uricase, an hepatic enzyme which degrades uric acid to allantoin, the blockade of this enzyme by oxonic acid is necessary.

Experimental Design

After one week on a low salt diet, weight-matched rats were randomly divided into four groups:
Group 1 (Vehicle (VH); n=6): These rats received a daily subcutaneous (SC) injection of olive oil, for 7 weeks.
Group 2 (Oxonic acid plus vehicle (OA); n=4): these rats received a daily SC injection of olive oil, 1 mg/kg, and a supplement of 2% oxonic acid in their chow, for 7 weeks.
Group 3 (Cyclosporine (CSA); n=6): these rats received a daily injection of cyclosporine 15 mg/kg, for 7 weeks.
Group 4 (Cyclosporine plus oxonic acid (CSA-OA); n=4): these rats received a daily injection of cyclosporine 15 mg/kg, and a supplement of 2% oxonic acid in their chow for 7 weeks.

After 7 weeks, rats were placed in individual metabolic cages for 24-hour urine collection. The following day, rats were anesthetized with xylazine and ketamine, serum was collected for creatinine and uric acid measurements, and both kidneys were obtained for histology evaluation. Biopsies were fixed in 10% formalin, 100% ethanol or Methyl Camoy's.

Functional Data

Serum and urine creatinine were measured by a standard picric acid method (Sigma Diagnostics creatinine kit, St. Louis, Mo.). Serum and urine uric acid were measured by a modified carbonate-phosphotungstate method [Henry, R. J., Sobel, C., and Kim, J., A modified carbonate phosphotungstate method for the determination of uric acid and comparison with the spectophotometric uricase method. Am J Clin Pathol 1957; 28:152.]. Fractional uric acid excretion and creatinine clearance were calculated by standard formulas. Cyclosporine levels were measured by high performance liquid chromatography (HPLC) of whole blood.

Drugs

Cyclosporine (Novartis) was diluted in olive oil to a final concentration of 15 mg/ml and injected SC in a dose of 15 mg/kg of body weight.

Renal Morphology and Immunohistochemistry

Methyl Carnoy's fixed tissue was processed and paraffin embedded, and 4 µm sections were stained with PAS reagents and hematoxilin-eosin. Alcohol-fixed tissue was processed and paraffin embedded, and 4 µm sections were stained for uric acid crystals by de Galantha's and Von Kossa stains. The positive control was kidney tissue from a rat with acute uric acid nephropathy, induced with oxonic acid and uric acid administration [Waisman, J., Bluestone, R., and Klinemberg, J. R., A preliminary report of nephropathy in hyperuricemic rats. Lab Invest 1974; 30:716, Bluestone, J., Waisman, J., Klinemberg, J. R., Chronic experimental hyperuricemia nephropathy. Biochemical and morphological characterization. Lab Invest 1975; 33(3): 273, and Waisman, J., Mwasi, L. M., Bluestone, R., and Klinemberg, J. R., Acute hyperuricemic nephropathy in rats. An electron microscopy study. Am J Pathol 1975; 81(2): 367.].

Methyl-Carnoy's fixed tissue sections were analyzed by indirect immunoperoxidase with primary antibodies against osteopontin (OP199, gift of C. Giachelli, University of Washington, Seattle, Wash.), monocytes and macrophages, (ED-1, Serotec, Oxford, UK) and collagen type III (Southern Biotechnology Associates Inc, Birmingham, Ala., USA).

Quantification of Morphologic Data

Interstitial fibrosis was scored semi quantitatively on biopsies stained with PAS and hematoxilin-eosin, using the following scoring system: zero=normal interstitium and tubules, 1=mild fibrosis with minimal thickening between the tubules, 2=moderate fibrosis with moderate interstitial thickening between the tubules, 3=severe fibrosis with severe interstitial thickening between the tubules.

The tubular expression of osteopontin (OPN), which is a sensitive marker of tubulointerstitial injury [Giachelli, C. M., Pichler, R., and Lombardi, D., Osteopontin expression in angiotensin II-induced tubulointerstitial nephritis. Kidney Int 1994; 45: 515, and Thomas, S. E., Lombardi, D., Giachelli, C., Bohle, A., and Johnson, R. J., Osteopontin expression, tubulointerstitial disease and essential hypertension. Am J Hypertens 1998; 11:954.], was calculated as the percentage (%) of renal cortex occupied by OPN-positive tubules [Johnson, R. J., Alpers, C. E., Yoshimura, A., et al., Renal injury from angiotensin II mediated hypertension. Hypertension 1992; 19: 464.], utilizing computer-assisted image analysis software (Optimas V6.2, Media Cybernetics, Silver Systems MD) and digitized images. The % area occupied by OPN positive tubules per 4 mm² field at 50× was measured and the mean % area calculated for each biopsy. The same method was used to quantify the interstitial expression of collagen III.

The mean number of interstitial macrophages (ED-1+cells/mm²) in each biopsy was calculated in a blinded manner by counting the total number of positive cells in 20 sequentially selected 0.25 mm² grids at 200× magnification. The number of macrophages per glomerular cross section (utilizing a minimum of 100 glomeruli per biopsy) was also determined.

Statistical Analysis

All values are expressed as mean±SD, unless otherwise stated. The differences between groups were compared with unpaired Student's t tests.

TABLE 3

Body weight, renal function and uric acid levels at 7 weeks of study

|  | Group 1 | Group 2 | Group 3 | Group 4 |
| --- | --- | --- | --- | --- |
| Weight (grams) | 422.2 ± 31.2 | 421.2 ± 28.8 | 357.2 ± 28.8$^{a,b}$ | 351.2 ± 10.7$^{a,b}$ |
| Serum Uric Acid (mg/dl) | 1.62 ± 0.31 | 4.08 ± 1.22$^a$ | 3.15 ± 0.85$^a$ | 5.90 ± 1.55$^{a,b,c}$ |
| Urinary Uric Acid (mg/day) | 2.19 ± 0.66 | 5.06 ± 2.81$^a$ | 3.05 ± 1.00 | 4.74 ± 3.22$^a$ |
| Urate/creatinine (urine) | 0.20 ± 0.08 | 0.35 ± 0.27 | 0.18 ± 0.09 | 0.23 ± 0.13 |
| FE urate | 0.12 ± 0.06 | 0.11 ± 0.14 | 0.07 ± 0.04 | 0.06 ± 0.04 |
| Serum Creatinine (mg/dl) | 0.94 ± 0.24 | 0.88 ± 0.19 | 1.35 ± 0.52$^b$ | 1.42 ± 0.32$^b$ |

TABLE 3-continued

Body weight, renal function and uric acid levels at 7 weeks of study

|  | Group 1 | Group 2 | Group 3 | Group 4 |
|---|---|---|---|---|
| Creatnine Clearance (ml/min) | 1.39 ± 0.73 | 1.94 ± 0.73 | 0.96 ± 0.43[b] | 0.79 ± 0.29[b] |
| Cyclosporine (ng/dl) |  |  | 4560.0 ± 602.0 | 4765.0 ± 486.0 |

[a]$p < 0.05$ compared to Group 1;
[b]$p < 0.05$ compared to Group 2;
[c]$p < 0.05$ compared to Group 3.
FE urate = fractional excretion of uric acid Uric Acid Serum uric acid in control rats on a low salt diet was 1.6±0.3 mg/dl (Table 3). In rats receiving CSA alone, the uric acid levels were increased almost 2-fold, and were similar to the levels in vehicle rats in which uricase was blocked by oxonic acid (OA). Serum uric acid levels were highest in rats treated with CSA and oxonic acid (CSA-OA). (Table 3).

Urinary uric acid excretion was increased in rats fed oxonic acid (OA alone and CSA-OA groups). CSA treated rats (CSA alone and CSA-OA) had urate/creatinine ratios comparable to normal controls and the fractional urate excretion tended to be lower than either vehicle or OA alone groups (p=0.06). (Table 3).

Cyclosporine Levels

CSA was measured by HPLC in whole blood at 7 weeks. No difference in CSA levels was observed between CSA and CSA-OA rats. (Table 3).

Renal Function

Glomerular filtration rate (GFR) evaluated by serum creatinine and creatinine clearance, were reduced in both CSA and CSA-OA groups, but no statistical difference was observed between CSA and CSA-OA groups (Table 3).

Histological Analysis

Tubulointerstitial and Micro Vascular Changes

Figure 9A:
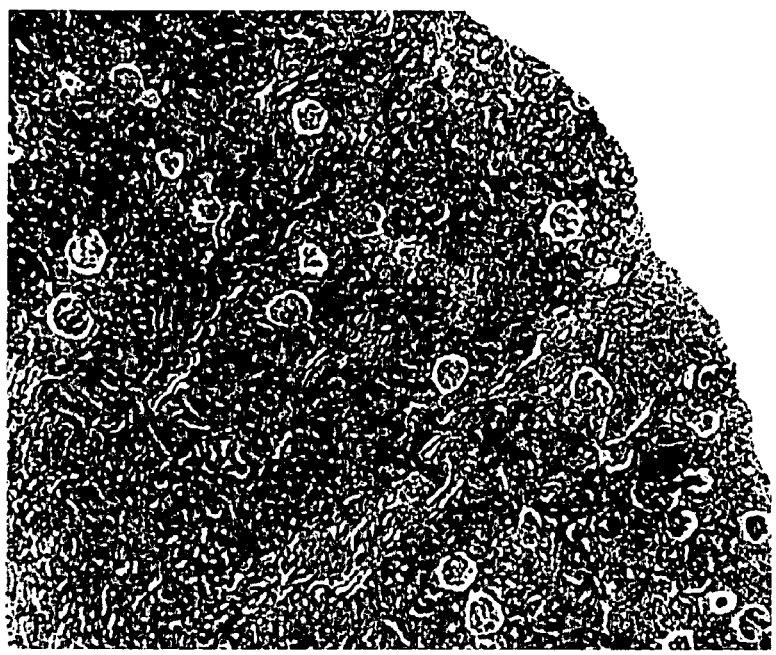
FIG. 9—Hyperuricemia exacerbates chronic cyclosporine nephropathy. Cyclosporine alone results in classic chronic tubulointerstitial disease [A], which is worse in rats that are also hyperuricemic [B](striped fibrosis indicated by arrows). Similarly, Cyclosporine-Oxonic Acid rats show greater osteopontin expression [D], macrophage infiltration [F] and type III collagen deposition [H], compared to respective controls [C,E,G]. (Magnification: hematoxilin-eosin ×50, OPN× 25, ED-1×100, type III collagen×50).
Figure 9B:
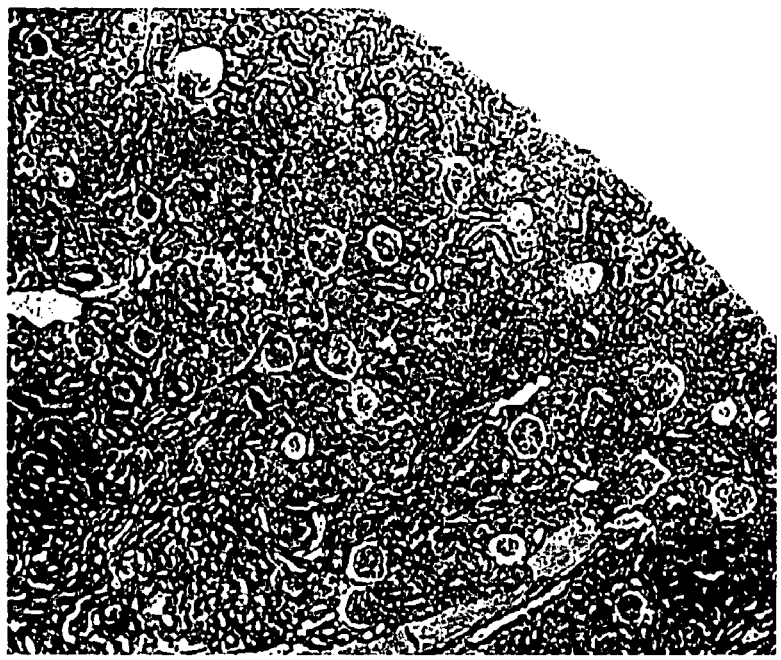

Rats treated with CSA for 7 weeks displayed classic histological findings of chronic CSA nephropathy, with arteriolar hyalinosis, tubular dilatation and atrophy in a stripped pattern extending from medulla to cortex (FIG. 9A). Similar histological findings were observed in CSA-OA rats, except that the changes were more severe, including arteriolar hyalinosis (61.8% vs 44.8%, CSA vs. CSA-OA, p<0.05)(FIG. 9B). In contrast, no significant tubulointerstitial changes were noted by light microscopy of PAS stained sections from VEH or OA alone rat kidneys.

Osteopontin Expression

Figure 9C:
Figure 9D:

Osteopontin is a macrophage-adhesive protein that is expressed by tubules in CSA nephropathy and has been shown to correlate with the macrophage infiltration, tubulointerstitial fibrosis and renal function [Pichler, R., Franceschini N., Young, B. A. et al., Pathogenesis of cyclosporine nephropathy. Roles of angiotensin II and osteopontin. J Am Soc Nephrol 1995; 6: 1186.]. Whereas minimal osteopontin is expressed in normal (VEH) control rats, a significant increase was observed in rats treated with CSA (FIG. 9C). The highest expression was observed in CSA-OA treated rats (FIGS. 9D and 10).

Macrophage Accumulation

Figure 9E:
Figure 9F:
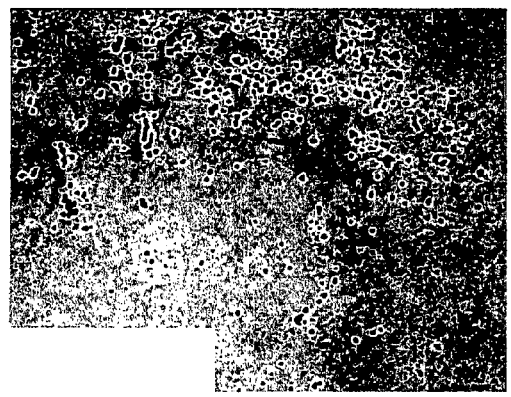

The marked increase in OPN expression in CSA and CSA-OA treated rats was associated with accumulation of ED-1+ macrophages in the interstitium (FIG. 9E). Similar to the findings of OPN, CSA-OA had a greater number of macrophages than CSA alone (395.6±92.5 vs. 271.9±43.4 ED-1+ cells/mm$^2$, p<0.05). In addition, CSA treated rats exhibited a mild glomerular macrophage accumulation, which was more pronounced in CSA-OA treated animals (1.8±0.5 vs. 3.5±1.7 ED-1+cells/glomerular cross section, p<0.05)(FIGS. 9E and 10).

Type III Collagen Deposition

Figure 9G:
Figure 9H:
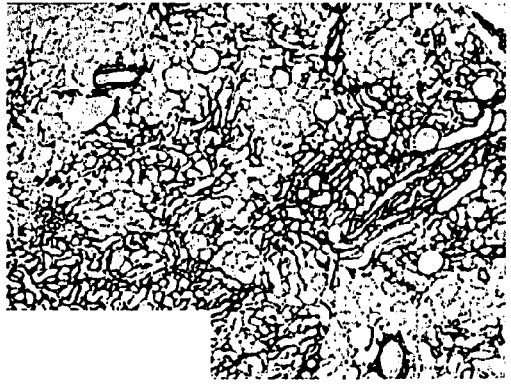
Figure 10A:
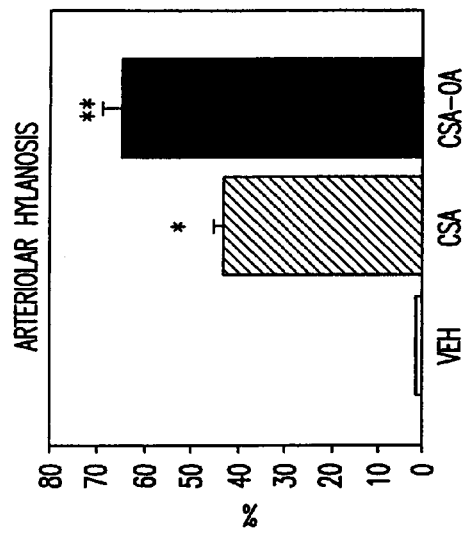
FIG. 10—Effect of Hyperuricemia alone and in combination with cyclosporine on renal interstitium. Group 3, cyclosporine treated rats (CSA, gray columns) presented increased interstitial fibrosis score [A], arteriolar hyalinosis [B], osteopontin expression [C], macrophage infiltration [D] and type III collagen deposition [E], compared to Group 1, vehicle treated rats (VEH, white columns). These findings are greatest in group 4, rats treated with both cyclosporine and oxonic acid (CSA-OA group, black columns). (*p<0.05 compared to VEH, **p<0.05 compared to VEH and CSA).
Figure 10B:
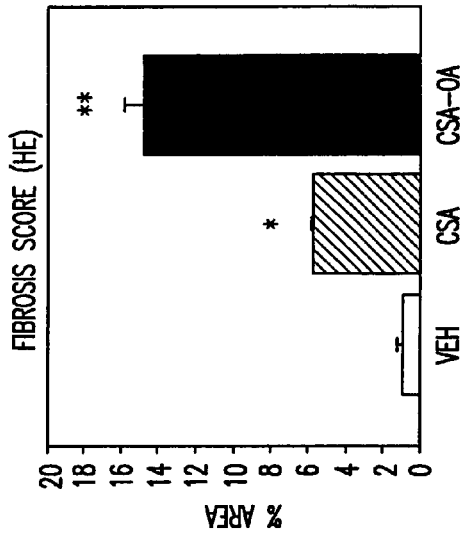
Figure 10C:
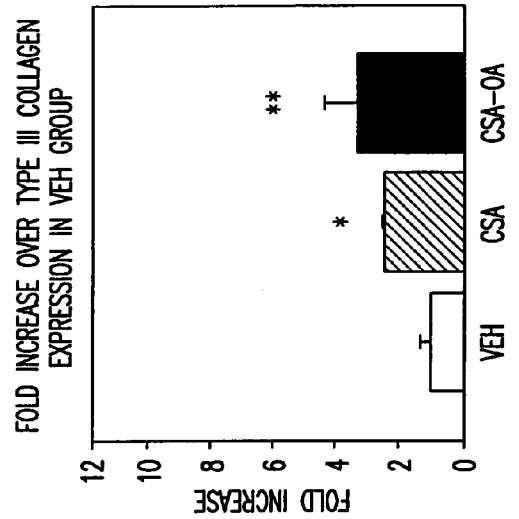
Figure 10D:
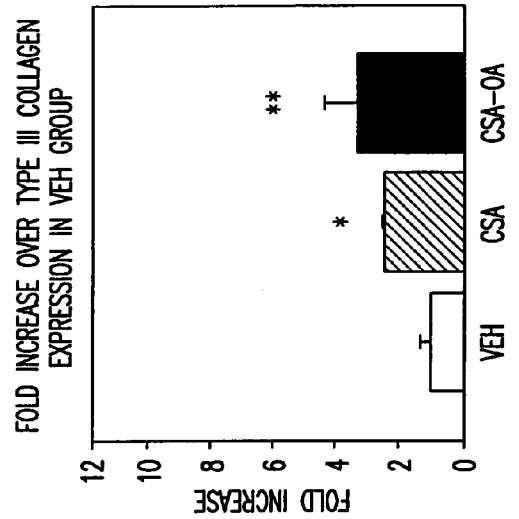
Figure 10E:
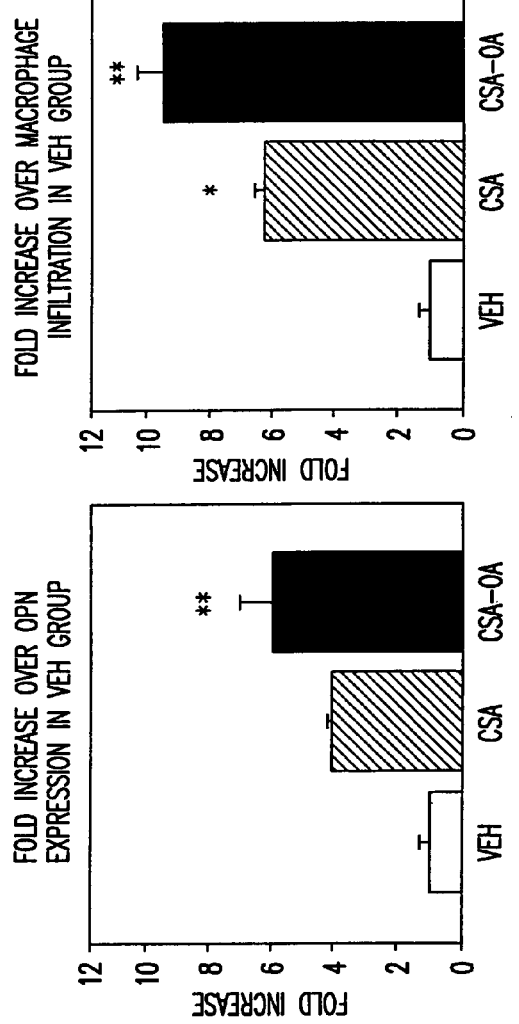

In normal kidney, type III collagen was minimally present in renal cortex, with slight accumulation around interlobular arteries and veins. In rats on CSA, type III collagen was increased in both the cortex and subcapsular area, and displayed a striped interstitial pattern similar to that observed by routine light microscopy (FIG. 9G). This general pattern was more severe in CSA-OA treated rats (FIGS. 9H and 10).

Crystal Deposition

In order to determine if the increased tubulointerstial injury observed in CSA-OA was associated with intrarenal crystal deposition, alcohol-fixed tissue was stained for uric acid crystals using both the De Galantha and modified Von Kossa stain. Whereas crystals could easily be identified in positive control tissue from rats with acute urate nephropathy induced by a combination of oxonic acid and uric acid, no crystals were present in any of the experimental groups.

Example 6

Uric Acid Excretion Activity (Excerpted from U.S. Pat. No. 5,260,322, Columns 41-42)

Twenty-four (24) male adults (25 to 48 years old, 161 cm to 187 cm tall, weighing 48 kg to 85 kg) were divided into 4 groups, 6 per group. Compound No. 9 [(COZAAR (losartan potassium)] was orally administered under hunger in the form of capsules in Example 2, in a definite dose (25 mg, 50 mg, 100 mg or 200 mg) per person, by varying the dose in each group. Further in order to examine influence of diet on uric acid excretion increasing activity of Compound No. 9, the capsule of Example 2 containing 100 mg of Compound No. 9 was orally administered at 2 weeks after the test under hunger was completed. Concentration of uric acid in urine and blood was determined by the uricase-POD method at every definite period of time after the administration. The results are shown in Tables 11 through 14.

As is clear from Tables 11 through 14, the concentration of uric acid in serum decreased in 4 hours after medication dose-dependently. However, a tendency that the uric acid concentration was recovered to the concentration level prior to medication was noted 24 hours after. On the other hand, when medicated after meals, the concentration of uric acid in serum was kept as it decreased even 24 hours after.

The uric acid concentration in urine dose-dependently increased from 0 to 4 hours by administering Compound No. 9 in doses of 25 mg, 50 mg and 100 mg per person. In the dose of 200 mg, however, the uric acid concentration in urine did not increase dose-dependently but was kept almost constant. On the other hand, when medicated after meals, the uric acid concentration in urine increased in 0 to 8 hours.

The foregoing results reveal that the non-peptide type compounds having an angiotensin II receptor-antagonizing activity in accordance with the present concentration in blood and increasing excretion of uric acid into urine. Accordingly, the non-peptide type compounds having an angiotensin II receptor-antagonizing activity in accordance with the present invention are useful as drugs for the prevention or treatment of hyperuricemia.

TABLE 11

Change of uric acid concentration in serum with passage of time when administered in hunger

| Time (hr) | Dose (mg/man) Concentration of Uric Acid (mg/dl) | | | |
|---|---|---|---|---|
| | 25 | 50 | 100 | 200 |
| 0 (when administered) | 5.2 ± 0.5 | 6.1 ± 1.4 | 5.9 ± 0.9 | 5.6 ± 0.7 |
| 4 | 4.8 ± 0.6 | 5.3 ± 1.3 | 4.6 ± 0.7 | 4.3 ± 0.9 |
| 24 | 4.6 ± 0.6 | 5.6 ± 1.4 | 5.2 ± 0.8 | 5.0 ± 0.9 |

TABLE 12

Change in uric acid concentration in serum with passage of time after meal

| Time (hr) | Dose 100 mg/man Concentration of Uric Acid (mg/hr) |
|---|---|
| 0 (when administered) | 5.8 ± 1.1 |
| 4 | 4.9 ± 1.0 |
| 24 | 4.7 ± 0.9 |

TABLE 13

Change of uric acid excretion in urine with passage of time when administered in hunger

| Time (hr) | Dose (mg/man) Concentration of Uric Acid (mg/hr) | | | |
|---|---|---|---|---|
| | 25 | 50 | 100 | 200 |
| 0-4 | 43.0 ± 24.5 | 52.8 ± 4.3 | 81.2 ± 15.7 | 78.7 ± 15.3 |
| 4-8 | 32.4 ± 14.7 | 42.8 ± 8.5 | 36.4 ± 7.7 | 25.4 ± 6.6 |
| 8-12 | 28.7 ± 13.6 | 39.1 ± 4.4 | 30.1 ± 6.8 | 19.6 ± 5.2 |
| 12-24 | 19.7 ± 9.9 | 22.2 ± 3.8 | 19.2 ± 4.2 | 13.4 ± 2.3 |
| 24-40 | 33.2 ± 21.9 | 26.6 ± 5.4 | 28.0 ± 7.2 | 21.0 ± 3.0 |

TABLE 14

Change in uric acid excretion in urine with passage of time after meal

| Time (hr) | Dose 100 mg/man Concentration of Uric Acid (mg/hr) |
|---|---|
| 0-4 | 75.9 ± 19.0 |
| 4-8 | 59.0 ± 3.8 |
| 8-12 | 31.8 ± 4.5 |
| 12-24 | 19.7 ± 2.5 |
| 24-40 | 29.5 ± 4.1 |

What is claimed is:

1. A method for treating hypertension in a subject in need thereof, said method comprising administering to the subject a therapeutically effective amount of allopurinol, or a pharmaceutically acceptable salt thereof.

* * * * *

UNITED STATES PATENT AND TRADEMARK OFFICE
CERTIFICATE OF CORRECTION

PATENT NO. : 7,799,794 B2  
APPLICATION NO. : 09/892505  
DATED : September 21, 2010  
INVENTOR(S) : Salah Kivlighn et al.

Page 1 of 1

It is certified that error appears in the above-identified patent and that said Letters Patent is hereby corrected as shown below:

In the specification, please insert the following paragraph at column 1, line 9 after the reference to related applications.

--STATEMENT OF GOVERNMENT SUPPORT

This invention was made with government support under DK047659 awarded by the National Institutes of Health. The government has certain rights in the invention.--

Signed and Sealed this
Fifteenth Day of July, 2014

Michelle K. Lee
*Deputy Director of the United States Patent and Trademark Office*